(12) United States Patent
Ohta et al.

(10) Patent No.: US 7,956,339 B2
(45) Date of Patent: Jun. 7, 2011

(54) SINGLE-SIDED LATERAL-FIELD AND PHOTOTRANSISTOR-BASED OPTOELECTRONIC TWEEZERS

(75) Inventors: Aaron Ohta, Honolulu, HI (US); Pei-Yu Chiou, Los Angeles, CA (US); Hsan-Yin Hsu, Berkeley, CA (US); Arash Jamshidi, Berkeley, CA (US); Ming-Chiang Wu, Moraga, CA (US); Steven L. Neale, Dunfermline (GB)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 12/565,984

(22) Filed: Sep. 24, 2009

(65) Prior Publication Data

US 2010/0101960 A1    Apr. 29, 2010

Related U.S. Application Data

(63) Continuation of application No. PCT/US2008/058701, filed on Mar. 28, 2008.

(60) Provisional application No. 60/943,103, filed on Jun. 11, 2007, provisional application No. 60/909,845, filed on Apr. 3, 2007, provisional application No. 60/908,452, filed on Mar. 28, 2007.

(51) Int. Cl.
*G01N 27/447*    (2006.01)
(52) U.S. Cl. ............... 250/559.04; 250/551; 250/208.1; 204/547; 204/643
(58) Field of Classification Search .......... 250/559.04, 250/551, 208.1; 204/547, 643
See application file for complete search history.

(56) References Cited

U.S. PATENT DOCUMENTS

| | | | |
|---|---|---|---|
| 4,758,526 A | 7/1988 | Thalheimer | |
| 5,707,502 A | 1/1998 | McCaffrey et al. | |
| 6,798,033 B2 | 9/2004 | Chao et al. | |
| 6,872,588 B2 | 3/2005 | Chabinyc et al. | |
| 6,878,961 B2 | 4/2005 | Lyons et al. | |
| 6,903,432 B2 | 6/2005 | Reshotko et al. | |
| 6,958,132 B2 | 10/2005 | Chiou et al. | |
| 7,040,947 B2 | 5/2006 | Ashida et al. | |
| 7,070,684 B1 * | 7/2006 | Fuhr et al. .............. | 204/547 |
| 7,084,471 B2 | 8/2006 | Reshotko et al. | |
| 7,088,116 B1 | 8/2006 | Lin | |
| 7,092,046 B2 | 8/2006 | Feoktistov et al. | |
| 7,586,105 B2 * | 9/2009 | Molhave ............... | 250/440.11 |
| 7,612,355 B2 * | 11/2009 | Wu et al. .............. | 250/559.04 |
| 2003/0047676 A1 | 3/2003 | Grier et al. | |
| 2005/0161698 A1 | 7/2005 | Takayama et al. | |
| 2006/0163463 A1 | 7/2006 | Grier | |

OTHER PUBLICATIONS

Chiou, Pei Yu et al. "Massively parallel manipulation of single cells and microparticles using optical images"—nature, vol. 436, pp. 370-372, Jul. 21, 2005.
Chiou, Pei Yu et al. "Cell Addressing and Trapping Using Novel Optoelectronic Tweezers"—IEEE International Conference on Micro Electro Mechanical Systems (MEMS), 2004.

(Continued)

*Primary Examiner* — Seung C Sohn
(74) *Attorney, Agent, or Firm* — John P. O'Banion

(57) ABSTRACT

Described herein are single-sided lateral-field optoelectronic tweezers (LOET) devices which use photosensitive electrode arrays to create optically-induced dielectrophoretic forces in an electric field that is parallel to the plane of the device. In addition, phototransistor-based optoelectronic tweezers (PhOET) devices are described that allow for optoelectronic tweezers (OET) operation in high-conductivity physiological buffer and cell culture media.

37 Claims, 22 Drawing Sheets

OTHER PUBLICATIONS

Shah, Gaurav J. et al. Integrating Optoelectronic Tweezers for Individual Particle Manipulation with Digital Microfluidics Using Electrowetting-On-Dielectric (EWOD)—19th IEEE International Conference on Micro Electro Mechanical Systems, 2006.

Chiou, Pei Yu et al. "Continuous Optical Sorting of HeLa Cells and Microparticles Using Optoelectronic Tweezers"—IEEE/LEOS International Conference on Optical MEMS, 2005.

Ohta, Aaron T. et al. "Manipulation of live red and white blood cells via optoelectric tweezers"—International Conference on Bio-Nano-Informatics (BNI) Fusion, 2005.

Voldman, Joel, "Electrical Forces for Microscale Cell Manipulation"—Annu. Rev. Biomed. Eng., vol. 8, pp. 425-454, Mar. 29, 2006.

Neuman, Keir C. et al. "Characterization of Photodamage to *Escherichia coli* in Optical Traps"—Biophysics Journal, vol. 77, pp. 2856-2863, Nov. 1999.

* cited by examiner

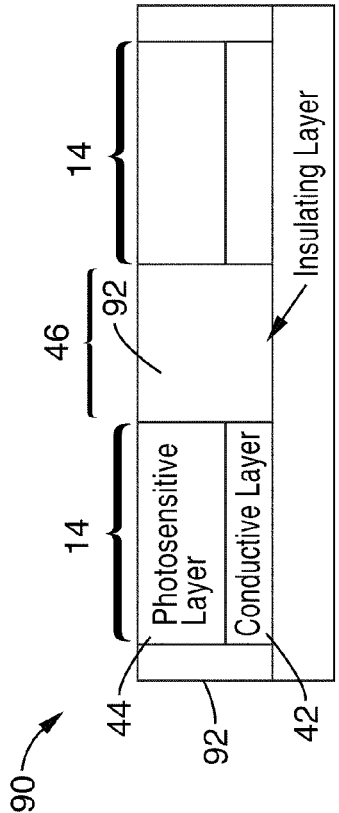
FIG. 5A
FIG. 5B
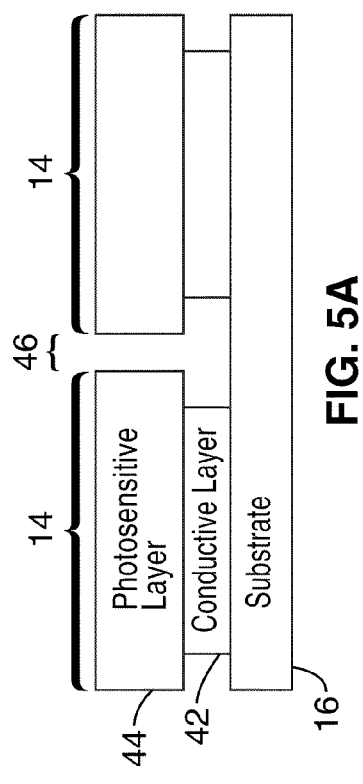
FIG. 5C
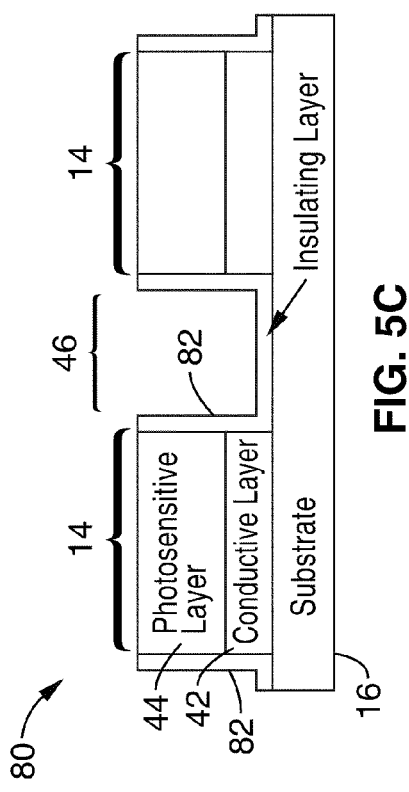
FIG. 5D

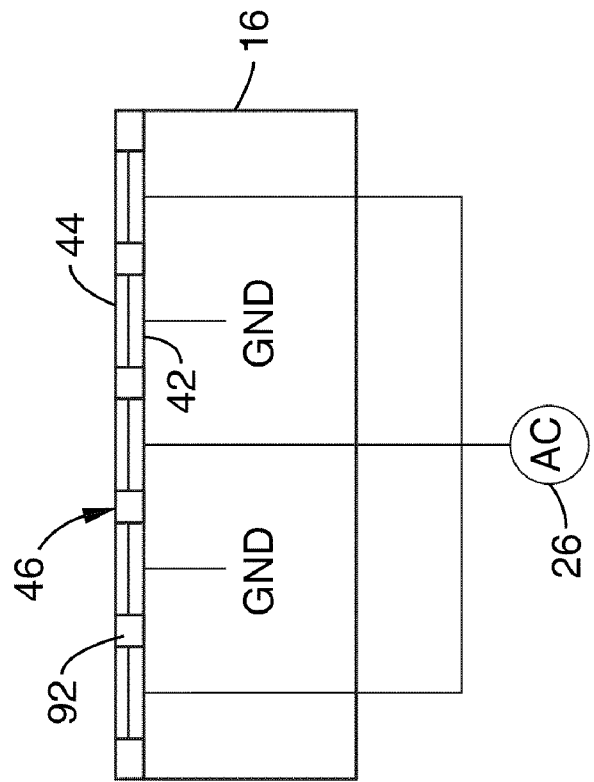
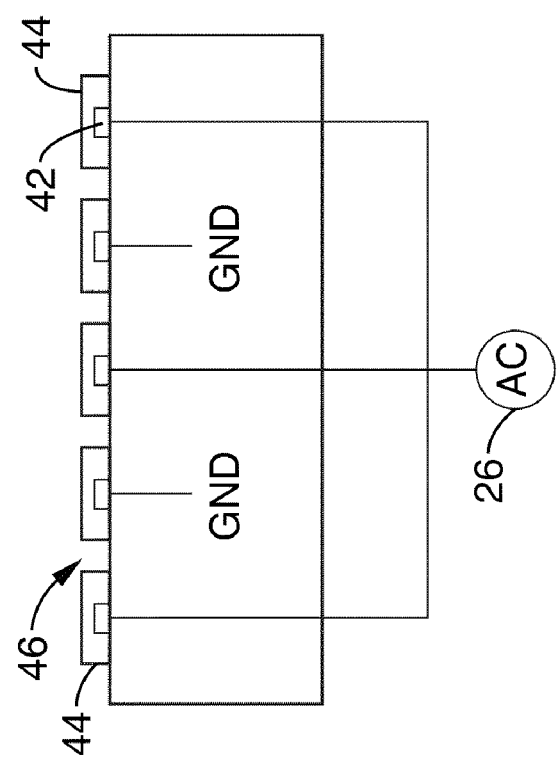

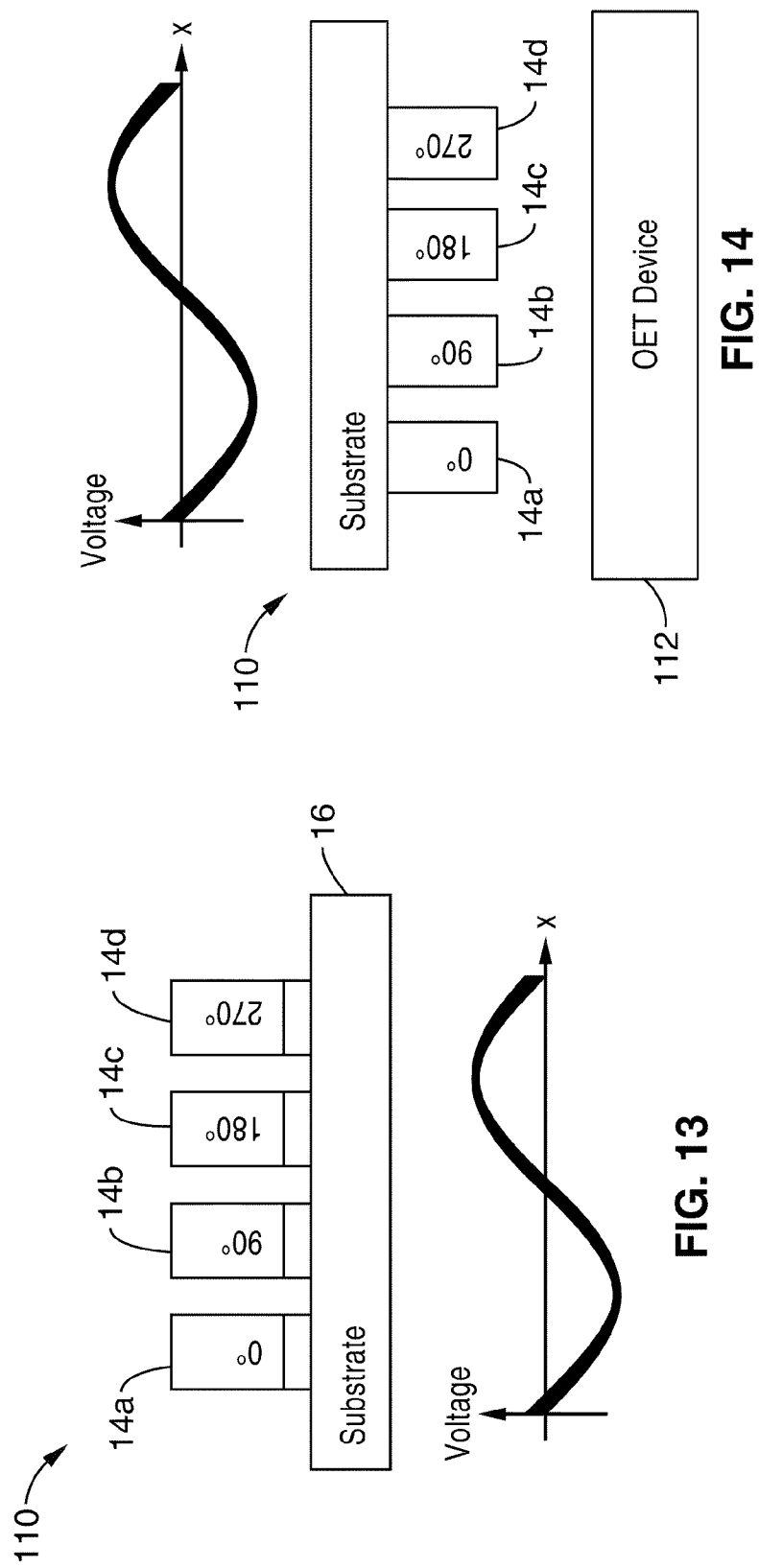

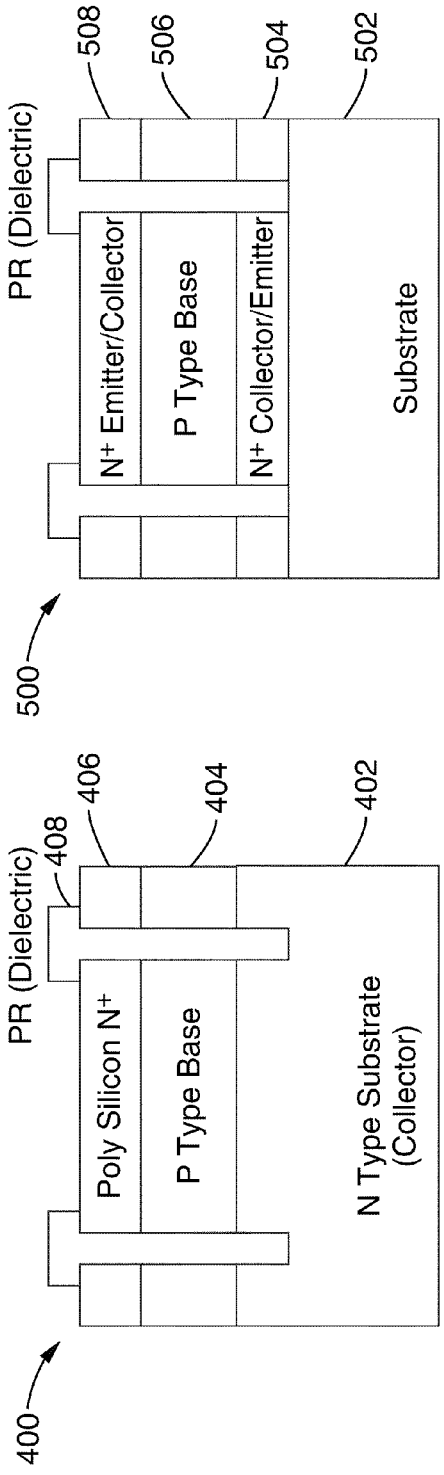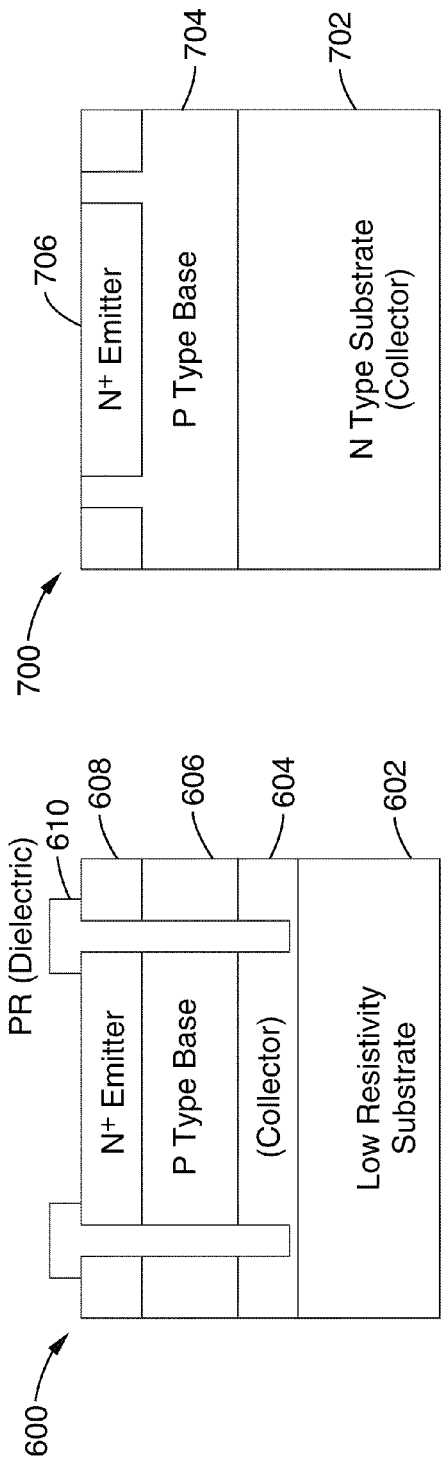
FIG. 24A
FIG. 24B
FIG. 24C
FIG. 24D

SINGLE-SIDED LATERAL-FIELD AND PHOTOTRANSISTOR-BASED OPTOELECTRONIC TWEEZERS

CROSS-REFERENCE TO RELATED APPLICATIONS

This application claims priority from, and is a 35 U.S.C. §111(a) continuation of, PCT international application serial number PCT/US2008/058701, filed on Mar. 28, 2008, incorporated herein by reference in its entirety, which claims priority to U.S. provisional patent application Ser. No. 60/943,103 filed on Jun. 11, 2007, incorporated herein by reference in its entirety, U.S. provisional patent application Ser. No. 60/909,845 filed on Apr. 3, 2007, incorporated herein by reference in its entirety, and U.S. provisional patent application Ser. No. 60/908,452, filed on Mar. 28, 2007, incorporated herein by reference in its entirety.

STATEMENT REGARDING FEDERALLY SPONSORED RESEARCH OR DEVELOPMENT

This invention was made with Government support under Grant No. NCC 2-1364, awarded by the Center for Cell Mimetic Space Exploration (CMISE), a NASA URETI. The Government has certain rights in this invention.

This application is also related to PCT International Publication No. WO 2008/119066 published on Oct. 2, 2008, incorporated herein by reference in its entirety.

INCORPORATION-BY-REFERENCE OF MATERIAL SUBMITTED ON A COMPACT DISC

Not Applicable

BACKGROUND OF THE INVENTION

1. Field of the Invention

This invention pertains generally to devices for manipulation of particles, and more particularly to optoelectronic tweezers.

2. Description of Related Art

Optically-induced dielectrophoresis, or optoelectronic tweezers (OET), provide a powerful, flexible method of manipulating microparticles and cells. In state of the art OET devices, the electric field is perpendicular to the photosensitive electrode surface. However, it is sometimes advantageous to have an electric field that is parallel to the photosensitive surface of the OET device. Rod-shaped particles, such as *E. coli* bacteria, align in parallel with the vertical electric field during the OET manipulation. In order to observe the long axis of rod-shaped particles, it is necessary to create an electric field in the lateral direction. Furthermore, such a device would only require a single, photosensitive electrode surface, allowing greater flexibility for OET device integration.

The following publications and patents provide additional background and are incorporated by reference in their entirety:

P. Y. Chiou, A. T. Ohta, and M. C. Wu, Nature, vol. 436, pp. 370-372, 2005.

P. Y. Chiou, W. Wong, J. C. Liao, and M. C. Wu, IEEE International Conference on Micro Electro Mechanical Systems (MEMS), 2004.

G. J. Shah, P. Y. Chiou, J. Gong, A. T. Ohta, J. B. Chou, M. C. Wu, and C-J. Kim, 19$^{th}$ IEEE International Conference on Micro Electro Mechanical Systems, 2006.

P. Y. Chiou, A. T. Ohta, M. C. Wu, IEEE/LEOS International Conference on Optical MEMS, 2005.

A. T. Ohta, et al., International Conference on Bio-Nano-Informatics (BNI) Fusion, 2005.

J. Voldman, "Electrical Force for Microscale Cell Manipulation", Annu. Rev. Biomed. Eng., vol. 8, pp. 425, 2006.

K. C. Neuman, E. H. Chadd, G. F. Liou, K. Bergman, and S. M. Block, "Characterization of photodamage to *Escherichia coli* in optical traps," Biophys. J., vol. 77, pp. 2856-2863, 1999.

U.S. Pat. No. 7,088,116; U.S. Pat. No. 7,092,046; U.S. Pat. No. 7,084,471; U.S. Pat. No. 6,958,132; U.S. Pat. No. 6,903,432; U.S. Pat. No. 6,878,961; U.S. Pat. No. 6,872,588; and U.S. Pat. No. 6,798,033.

BRIEF SUMMARY OF THE INVENTION

We have designed, fabricated, and demonstrated a new device for producing optically-controlled dielectrophoretic forces. Previous demonstrations of optically-induced dielectrophoresis, in optoelectronic tweezers (OET) devices, have used electrical fields that are perpendicular to the plane of the device, causing irregular or rod-shaped particles to align to the vertical electric field. Our new device, single-sided lateral-field optoelectronic tweezers (LOET), uses photosensitive electrode arrays to create optically-induced dielectrophoretic forces in an electric field that is parallel to the plane of the device. This allows rod-shaped microparticles such as bacteria and nanowires to align with the horizontal electric field, allowing the imaging of the long axis of the particles. This device also contains all of the necessary electrodes on a single substrate, unlike the OET device, which has two separate electrode surfaces. Thus, the LOET device enjoys a greater flexibility for integration with other microelectromechanical or microfluidic systems. The idea of photosensitive electrodes can also be used to create an OET device that utilizes traveling waves (spatially-varying electric fields).

In one embodiment, an LOET may comprise a first electrode and a second electrode spaced apart from the first electrode by a gap; a substrate layer supporting the electrodes; wherein each electrode comprises a conductive layer adjacent to the substrate layer and a photosensitive layer adjacent to the conductive layer; wherein the electrodes are configured to create optically-induced dielectrophoretic forces in an electric field that is parallel to the plane of the LOET.

In another embodiment, the LOET may comprise first and second arrays of photosensitive electrodes. In still another embodiment, the electrodes may be interdigitated.

In one embodiment, the conductive layer may undercut the photosensitive layer. In another embodiment, the photosensitive layer may surround the conductive layer. In another embodiment, a thin insulating layer may be positioned around the conductive layer. In another embodiment, an insulating layer may be positioned around the conductive layer and fill the electrode gaps.

In one embodiment, the LOET may comprise a photosensitive layer coated on an insulating substrate; a first electrode and a second electrode spaced apart from the first electrode by a gap; wherein each electrode comprises a conductive layer adjacent to the photosensitive layer; wherein the electrodes and photosensitive layer are configured to create optically-induced dielectrophoretic forces in an electric field that is parallel to the plane of the LOET. In another embodiment, the LOET may comprise first and second arrays of photosensitive electrodes. In still another embodiment, the electrodes may be interdigitated. In another embodiment, the electrodes may be coated by an electrically insulating layer.

In one embodiment, the LOET may include a cover layer spaced apart from and positioned adjacent the photosensitive layer, whereby a chamber for containing a liquid/particle solution is formed.

In addition, we demonstrate, for the first time, the OET operation in high-conductivity physiological buffer and cell culture media. To enable manipulation in highly conductive solution, a novel phototransistor-based optoelectronic tweezers (PhOET) device has been developed.

In one embodiment, a PhOET may comprise a cover layer; a substrate layer; a photoconductive layer between the cover layer and the substrate layer; and a liquid layer between the cover layer and the photoconductive layer; wherein the photoconductive layer comprises a phototransistor. In another embodiment, the PhOET may comprise a plurality of phototransistors separated by a dielectric gap.

In one embodiment, each phototransistor may have a vertical bipolar junction transistor structure. In one embodiment, each phototransistor may comprise a highly doped n-type emitter; a moderately doped p-type base; and a lowly doped n-type material as both the collector and the conductive substrate.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWING(S)

The invention will be more fully understood by reference to the following drawings which are for illustrative purposes only:

Figure 3:
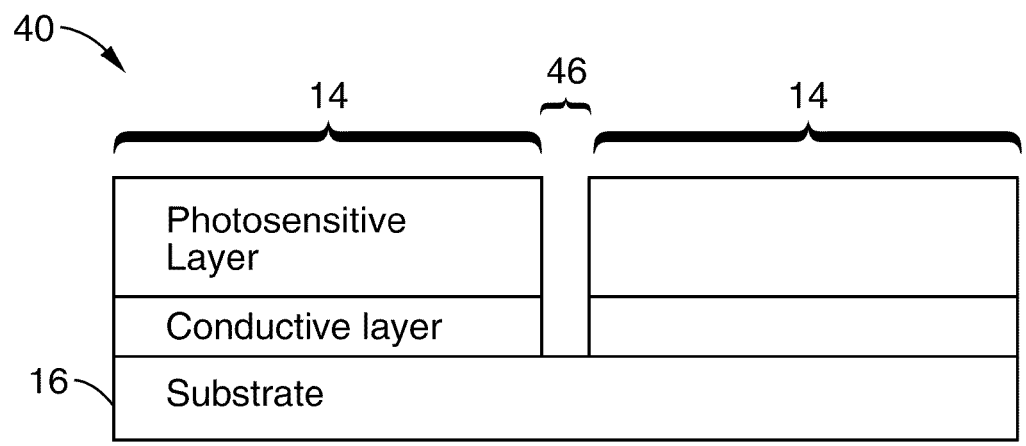
FIG. 3 is a generalized cross-sectional schematic view of an embodiment of an LOET device according to the present invention.

FIG. 5 contains cross-sectional schematic views of various conductive layer configurations in the LOET illustrated in FIG. 3.

FIG. 6 contains schematic diagrams of LOET electrode configurations corresponding to FIG. 5B and FIG. 5D, respectively.

FIG. 7 contains images illustrating simulated electric fields in an LOET according to the present invention.

FIG. 8 contains images showing nanowire trapping and transport in an LOET according to the present invention.

FIG. 9 contains images showing live Jurkat cell trapping and transport in an LOET according to the present invention.

Figure 10:
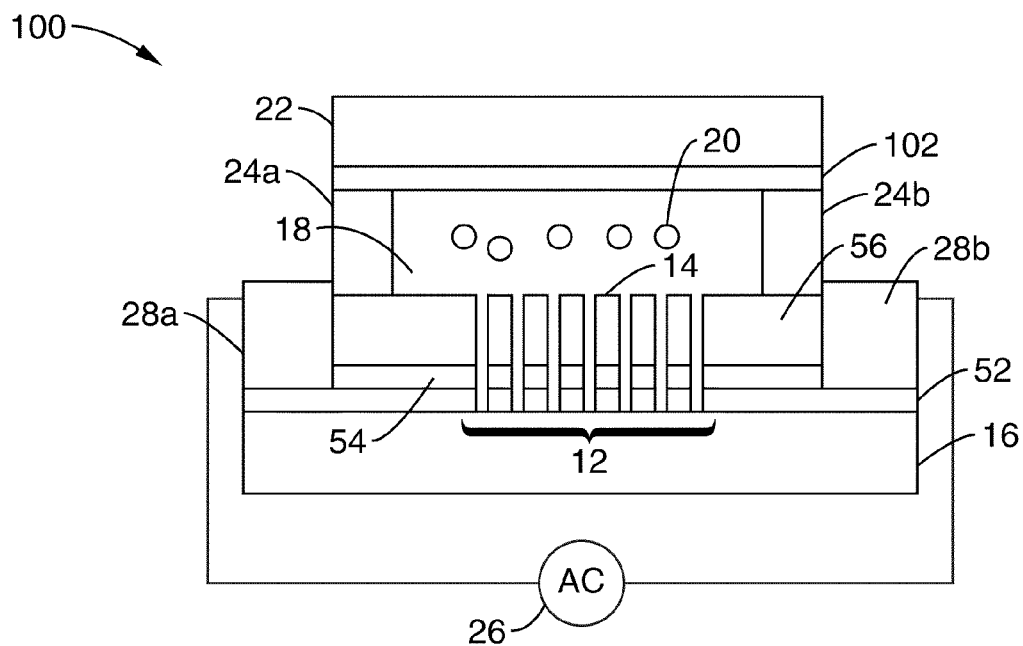

FIG. 10 is a cross-sectional schematic view of an embodiment of a LOET according to the present invention having a conductive opposing surface.

Figure 11:
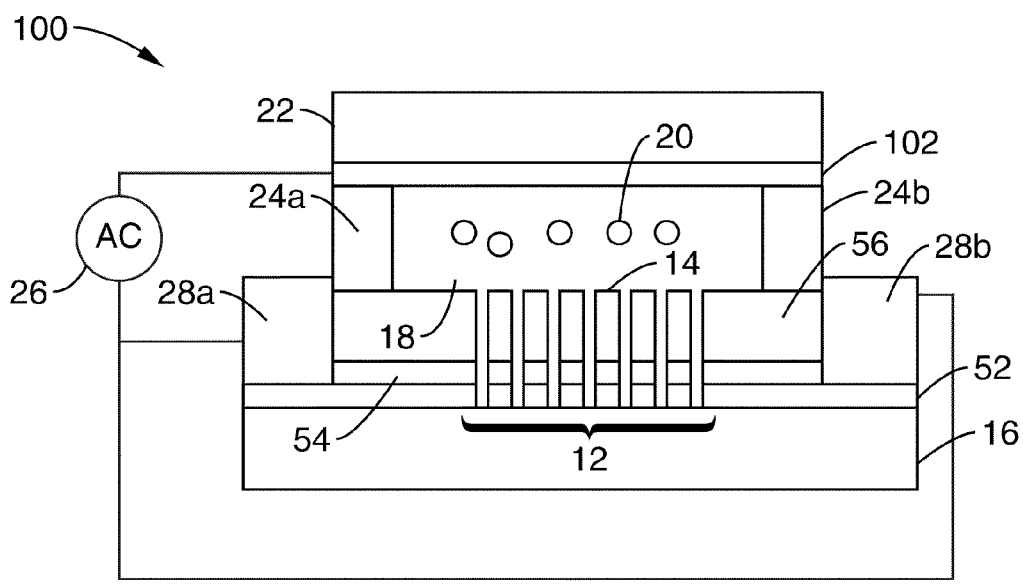

FIG. 11 is a cross-sectional schematic view of the LOET shown in FIG. 10 configured for conventional OET operation.

FIG. 12 contains images showing manipulation of polystyrene beads in an LOET according to the present invention configured for conventional OET operation.

FIG. 13 is a schematic of a traveling-wave OET device, using alternating-phase voltages applied to photosensitive electrodes to produce a spatially-varying electric field.

FIG. 14 is a schematic of a traveling-wave OET device, using alternating-phase voltages applied to a patterned upper electrode surface.

Figure 15A:
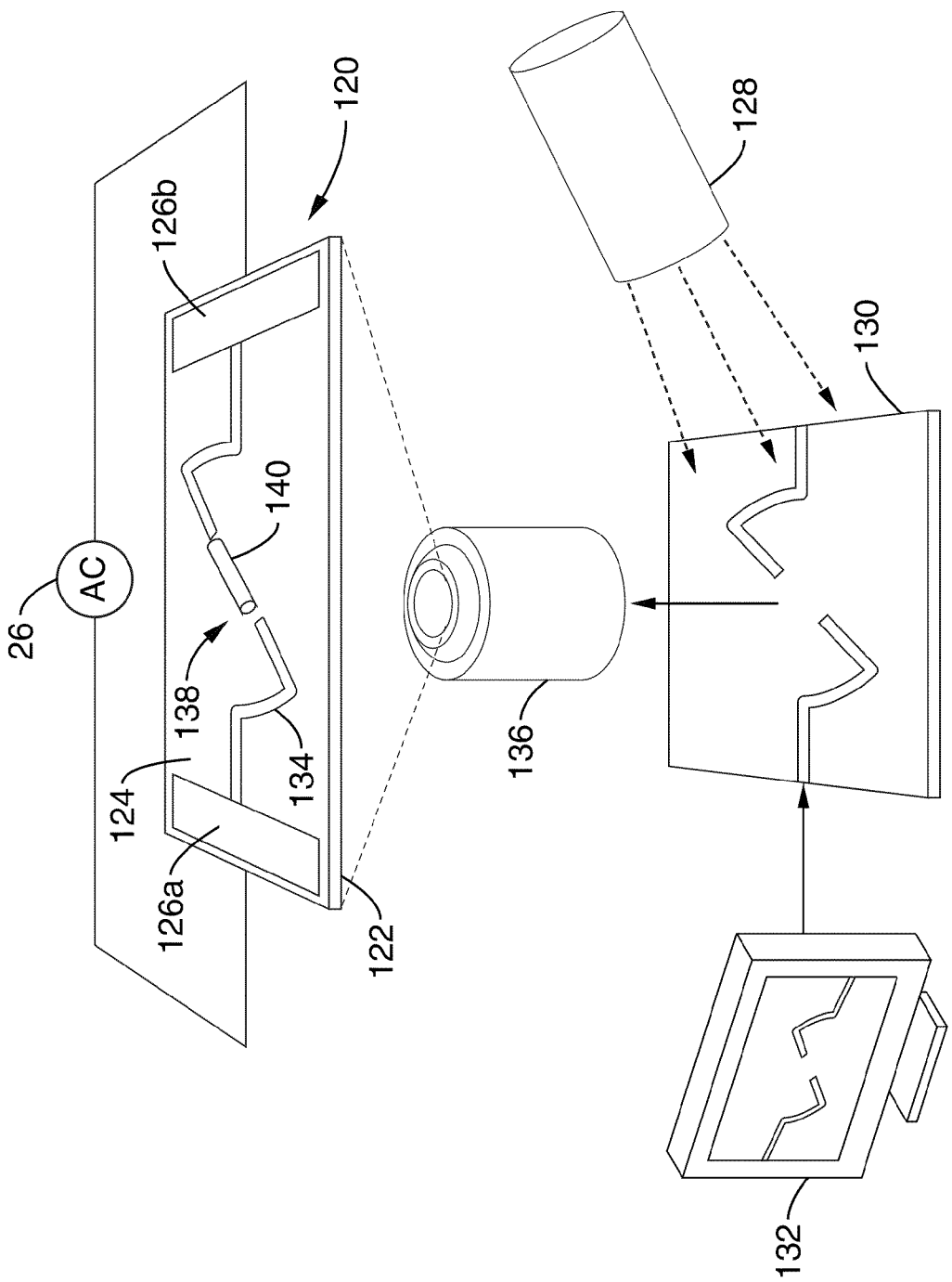
Figure 15B:
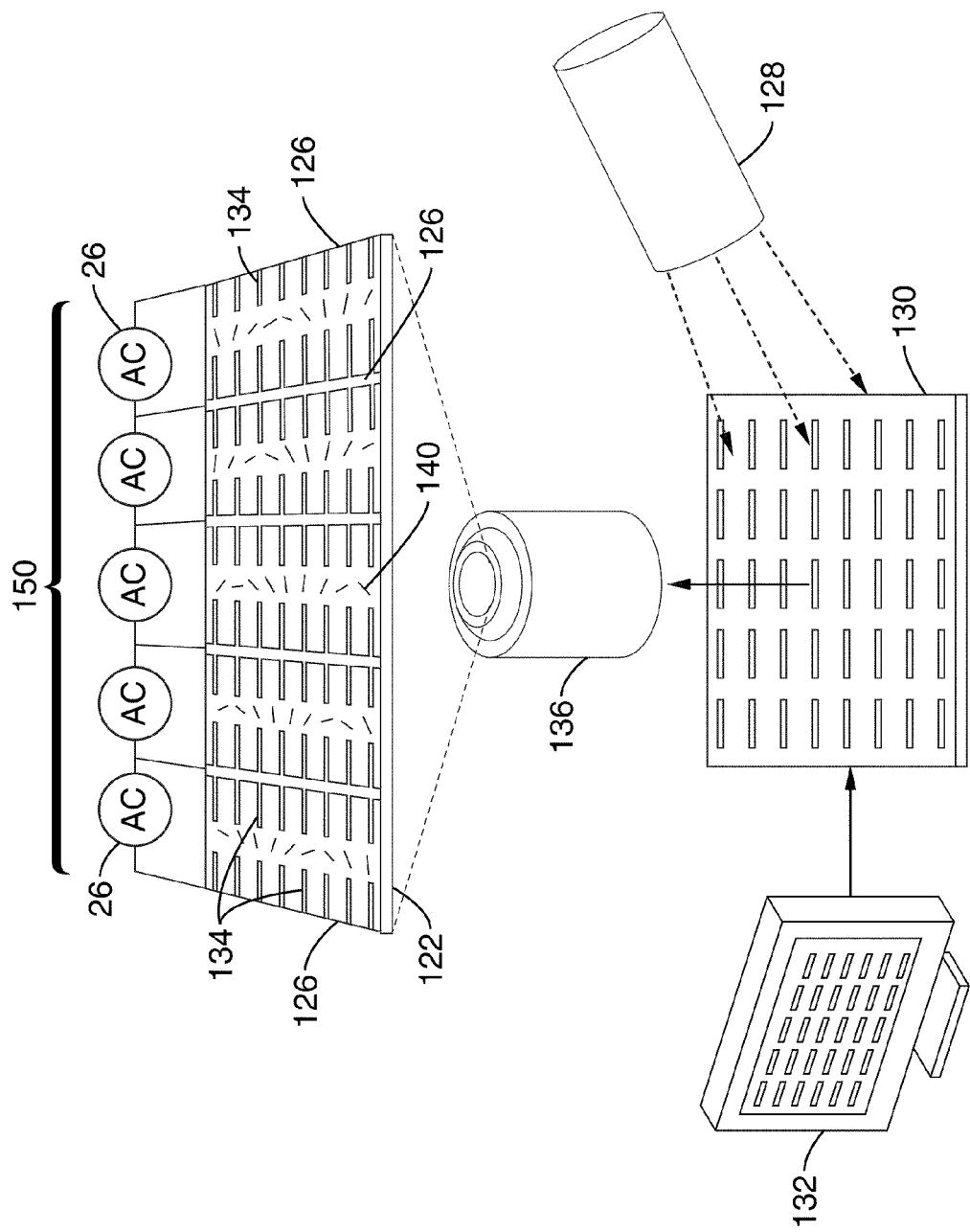

FIG. 15 shows a schematic of an LOET illustrating automated parallel assembly of nanowires (FIG. 15A) and illustrates a large number of LOET traps operating at the same time through computer-controlled DMD patterns (FIG. 15B).

FIG. 16 shows the substrate from FIG. 15 and how changing the light pattern, which acts as "virtual electrodes", can change both the position and the orientation of the nanowire.

FIG. 17 shows manipulation of nanowires using an embodiment of a LOET according to the invention.

Figure 18A:
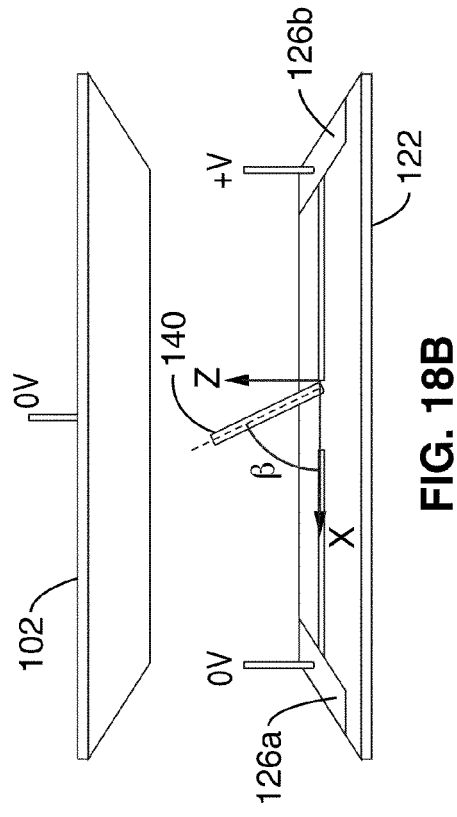
Figure 18B:
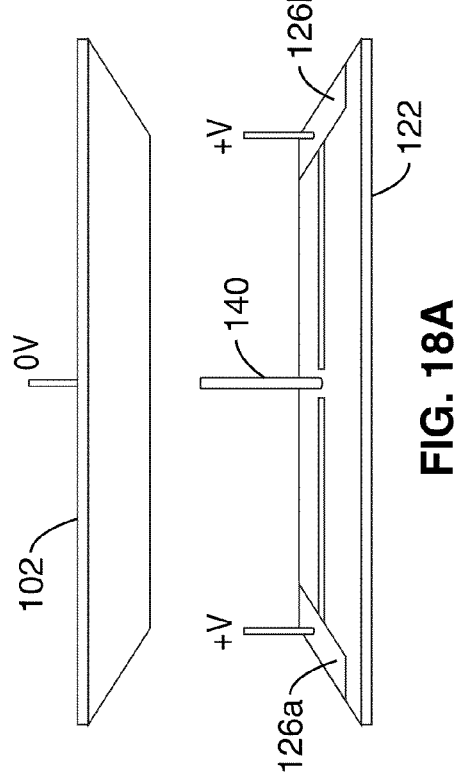
Figure 18C:
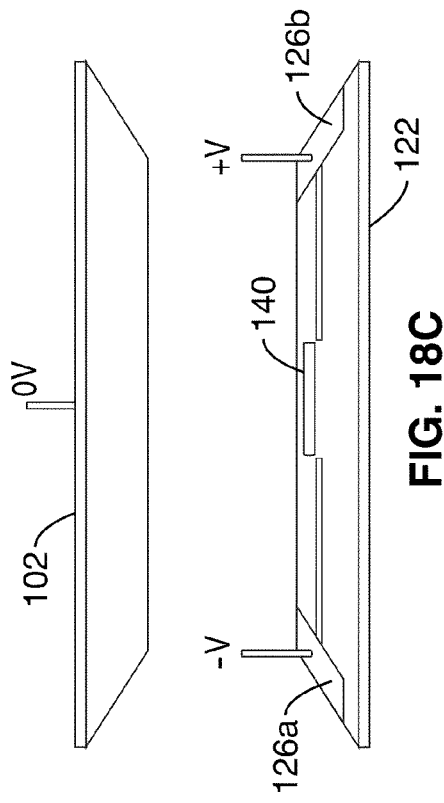

FIG. 18 illustrates vertical orientation control of a nanowire using an embodiment of a LOET according to the present invention.

Figure 19:
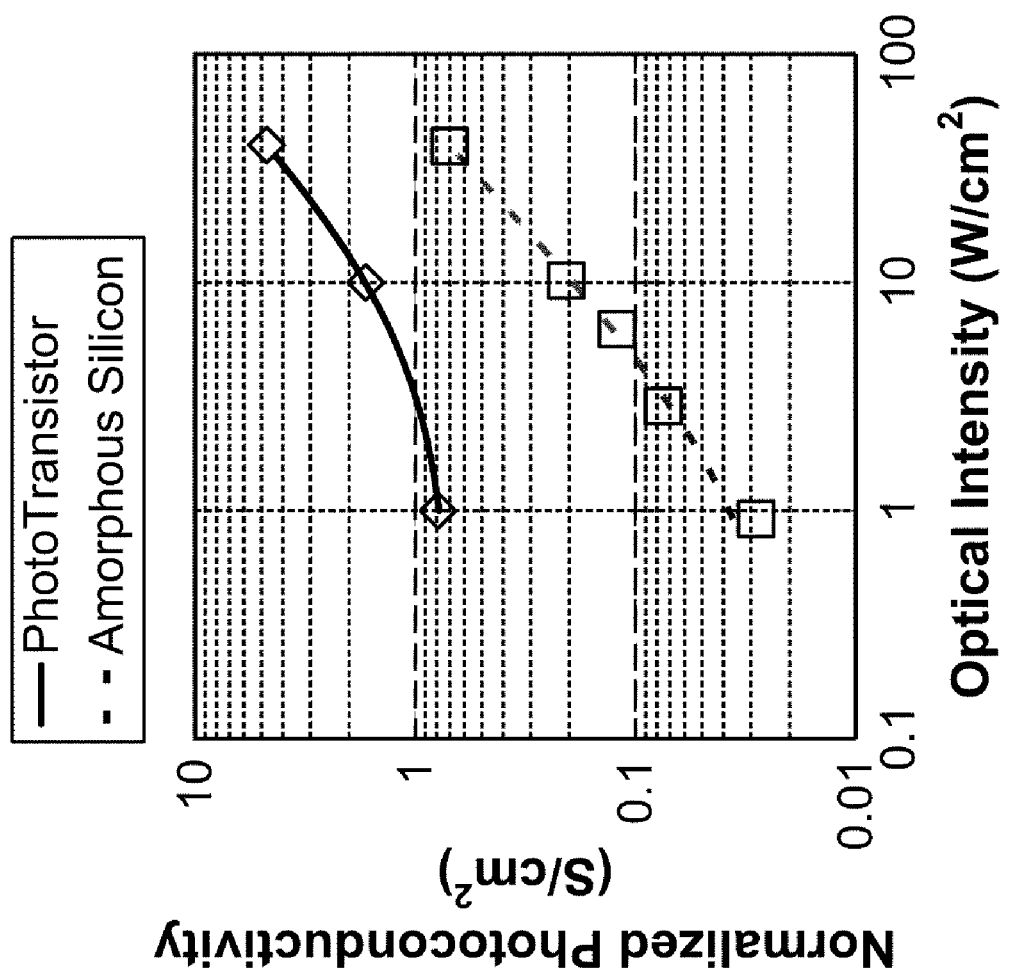

FIG. 19 is a graph showing normalized photoconductivity measurement of the phototransistor-base OET device and the amorphous silicon-based OET device.

Figure 20:
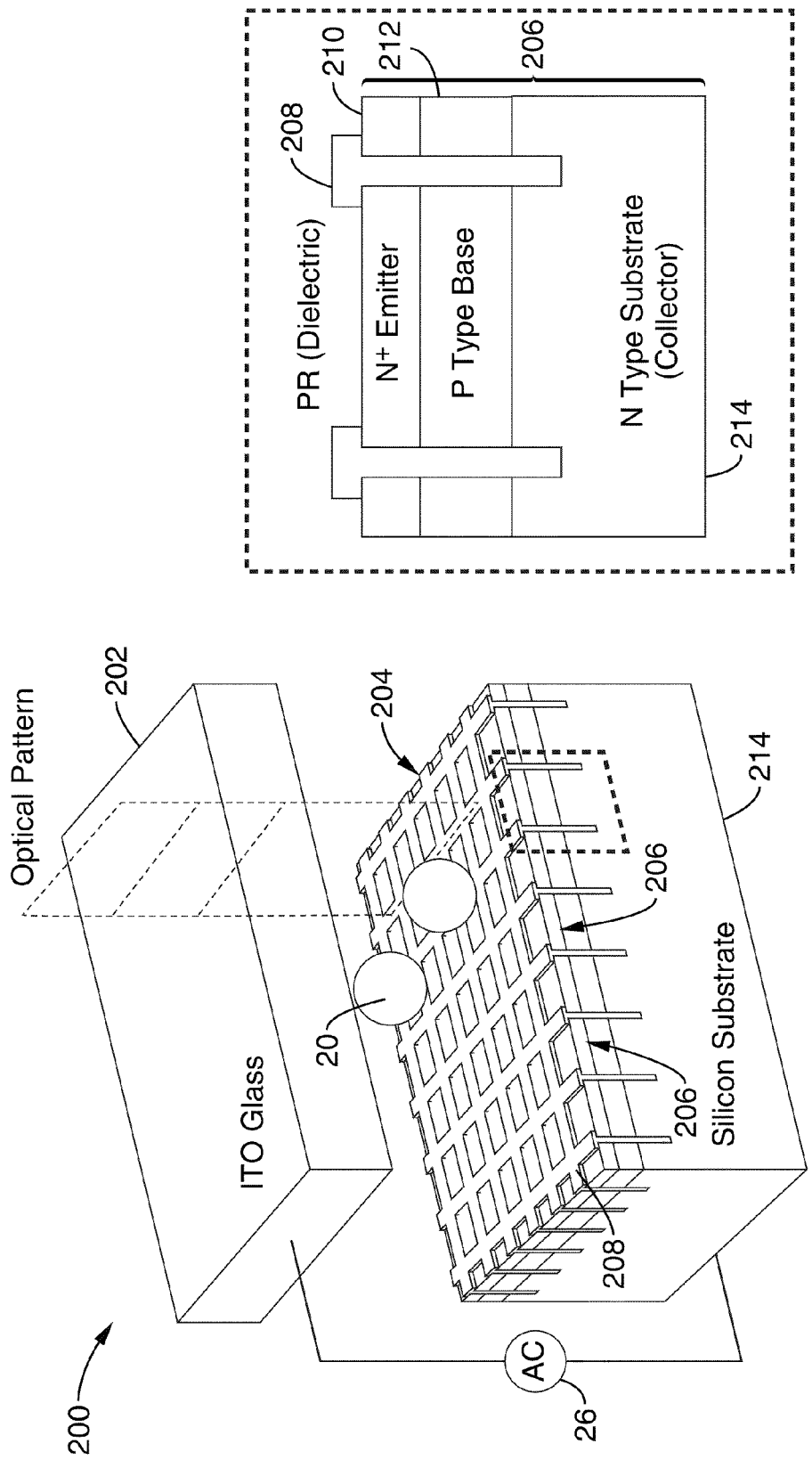

FIG. 20 schematically illustrates an embodiment of a phototransistor OET (PhOET) structure according to the present invention.

Figure 21:
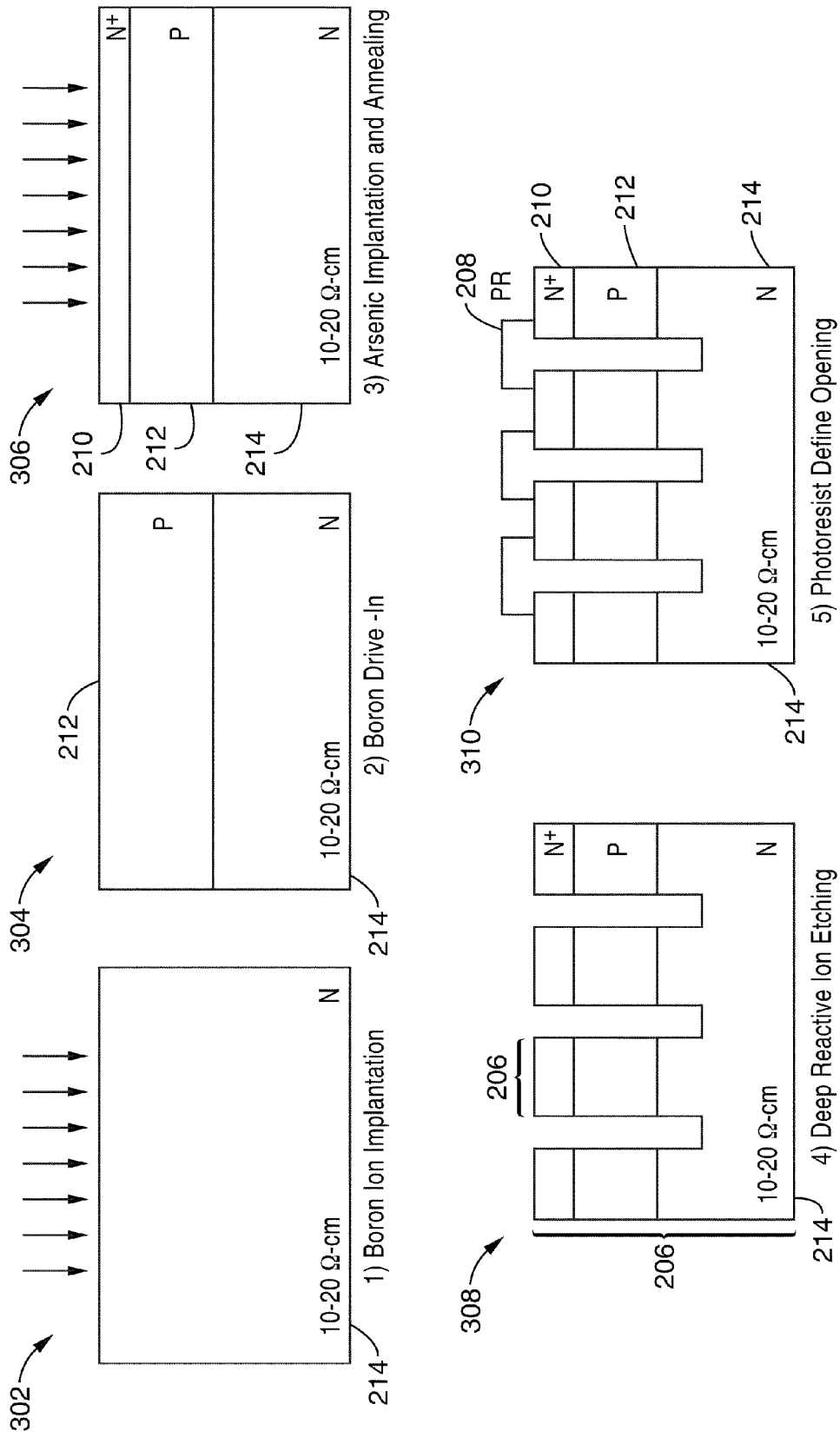

FIG. 21 is a flow chart of an embodiment of a PhOET fabrication process according to the present invention.

FIG. 22 contains images illustrating optical manipulation of two HeLa cells in PBS solution.

Figure 23A:
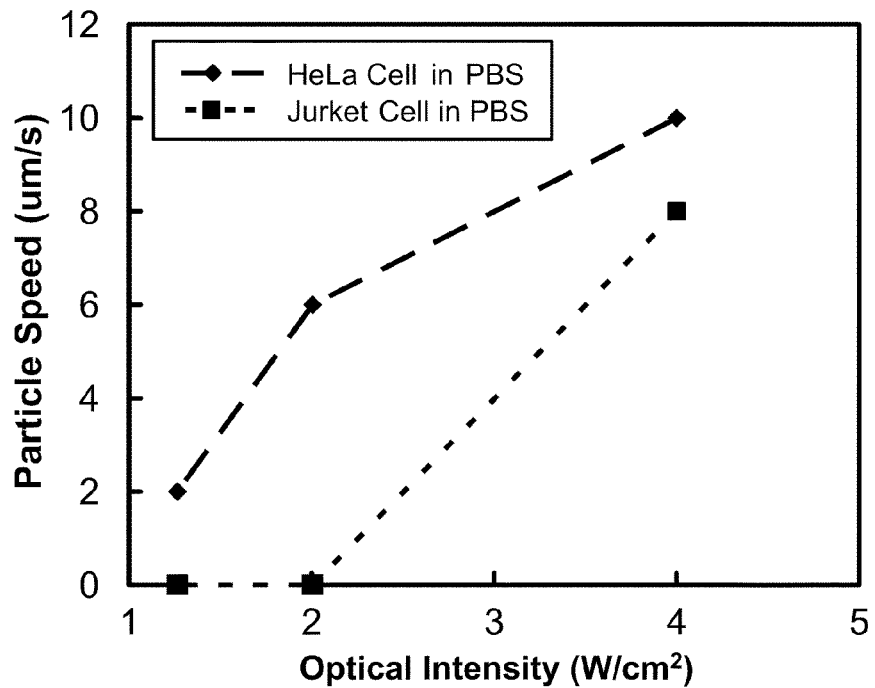
Figure 23B:
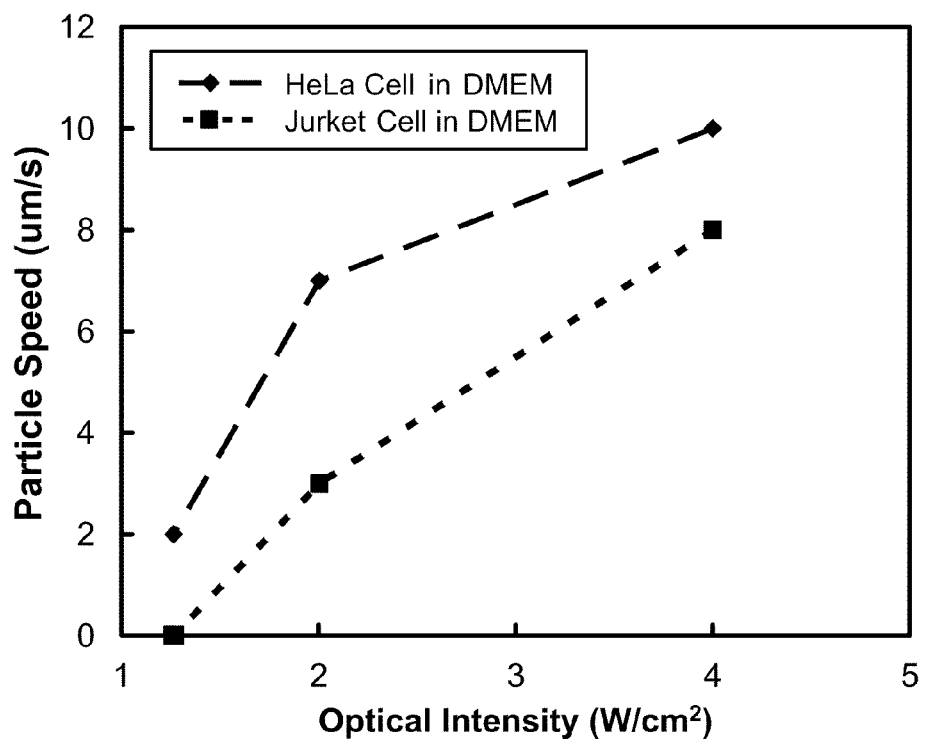

FIG. 23 contains graphs illustrating cell manipulation speed in phosphate-buffered saline (PBS) solution (FIG. 23A) and Delbecco's Modified Eagle Medium (DMEM) (FIG. 23B) as a function of optical Intensity.

FIG. 24 contains schematic cross-section views of various embodiments PhOET structures according to the present invention.

DETAILED DESCRIPTION OF THE INVENTION

1. Single-Sided Lateral-Field Optoelectronic Tweezers

An aspect of the present invention is a new design for an optoelectronic tweezers (OET) device that creates lateral electric fields on a single-sided device. This lateral-field OET device (LOET) retains the flexibility and capabilities of a conventional OET device, while offering advantages for the manipulation of rod-shaped particles. The LOET device also promises to facilitate the integration of OET manipulation with other MEMS technology, such as electrowetting-on-dielectric (EWOD) devices.

Figure 2:
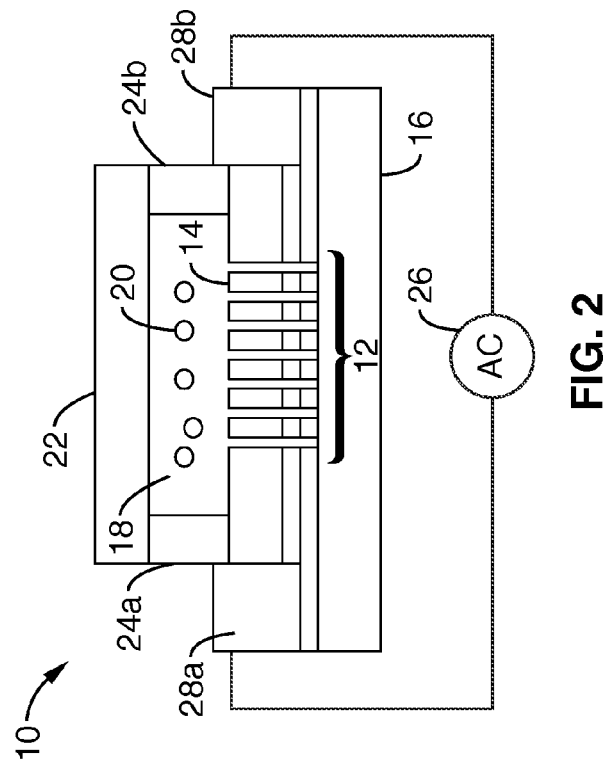
FIG. 2 is a schematic side view of the interdigitated LOET device according to the present invention, showing the chamber that contains the liquid/particle solution.
Figure 1:
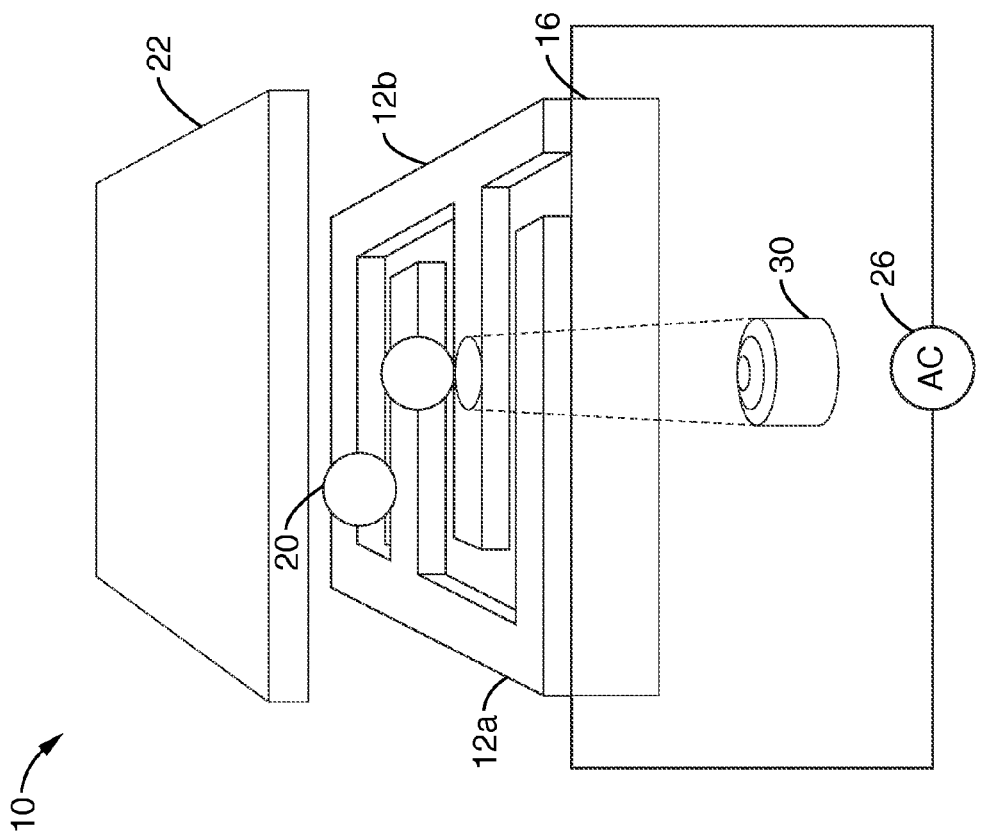
FIG. 1 is a schematic of an embodiment of an LOET device according to the present invention with interdigitated electrode arrays, and showing the device in combination with an optical source and AC source.

Referring first to FIG. 1 and FIG. 2, an embodiment 10 of the inventive LOET device comprises interdigitated arrays 12a, 12b of photosensitive electrodes 14 on a substrate 16. A liquid/particle layer 18 containing cells, bioparticles, microparticles, or nanoparticles 20 is placed on the electrodes. A cover layer 22 may be placed over the liquid layer 18 and supported with spacers 24 to form a chamber for minimizing evaporation. In addition, this top cover layer may contain microfluidic channels. Note that the entire configuration may also be inverted, so that the cover layer is the lower layer, and the electrode layer is on the top. Also shown, but not part of the invention, is an AC source 26 placed across electrode pads 28a, 28b connected to the electrode arrays for creating an electrical field. Also, shown for context, but not part of the invention, is an optical source 30. Illumination of the electrodes causes actuation of OET force. Note that optical source can be on the top or bottom of the device. Note also that the electrode array(s) can be interdigitated as illustrated in FIG. 1 and FIG. 2, or arranged in another pattern that facilitates the creation of electric fields parallel to the plane of the device.

Example 1

An interdigitated LOET device as illustrated in FIG. 1 and FIG. 2 was created by depositing 100-nm of ITO on an insulating substrate 16. Other conductive materials may also be used. A 50-nm layer of highly-doped a-Si:H is deposited over the ITO, followed by a 1-µm-thick layer of intrinsic a-Si:H 14. Both a-Si:H layers are deposited by plasma-enhanced chemical vapor deposition. Electrode patterns 12 were etched into the a-Si:H layers by reactive ion etching. The patterns are transferred to the ITO layer by a wet acid etch. Electrical contact pads 28 were created by etching the a-Si:H layers down to the ITO layer, and adding conductive epoxy or another conductive material over the exposed ITO layer.

Referring now to FIG. 3, in a generalized embodiment 40, the device may comprise any type of conductive material 42 on the substrate 16, topped by a photosensitive layer 44 of varying thickness, with individual devices spaced apart by an electrode gap 46.

Example 2

Figure 4:
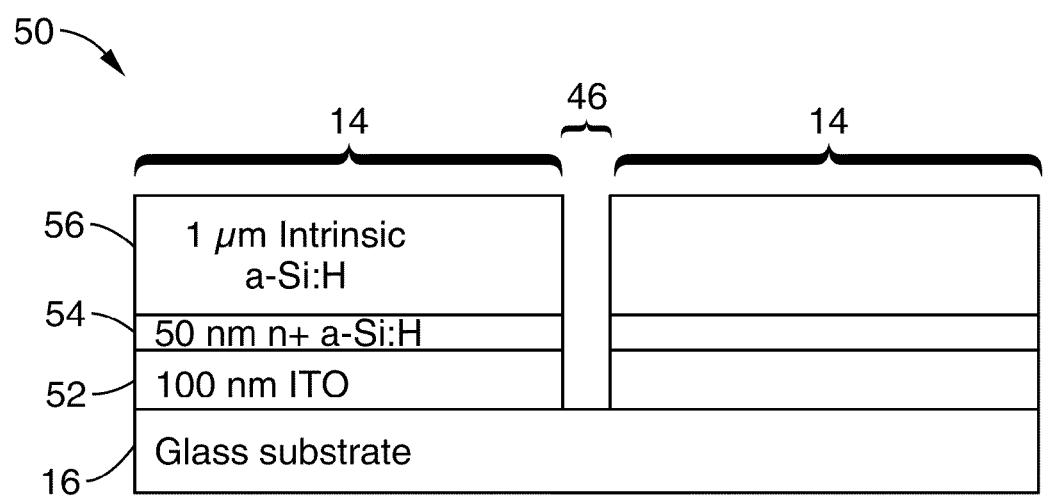
FIG. 4 is a cross-sectional schematic view of an embodiment of an LOET device according to the present invention.
Figure 7A:
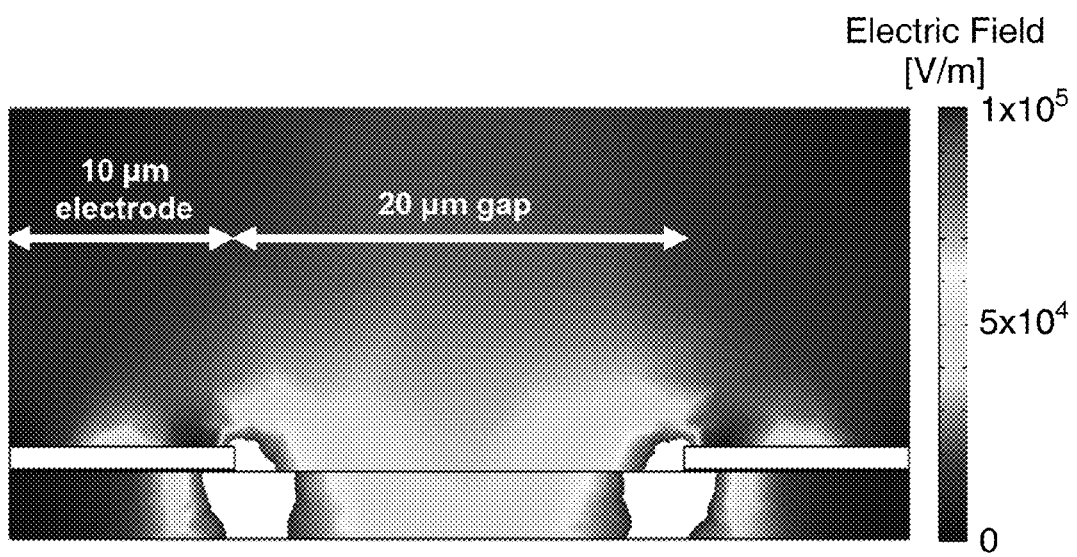
Figure 7B:
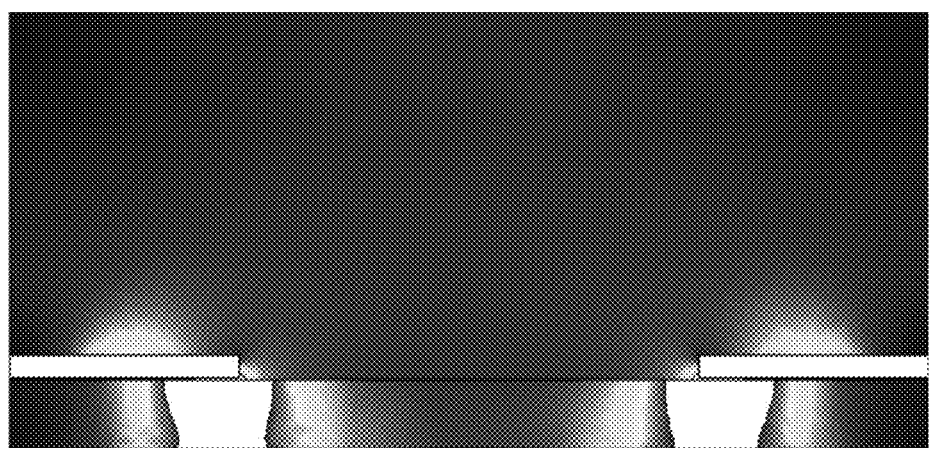
Figure 7C:
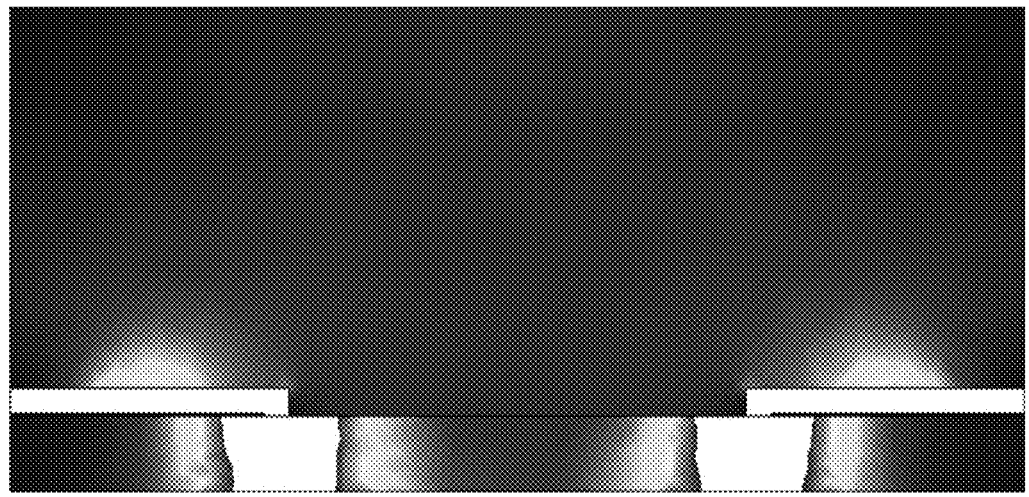
Figure 7D:
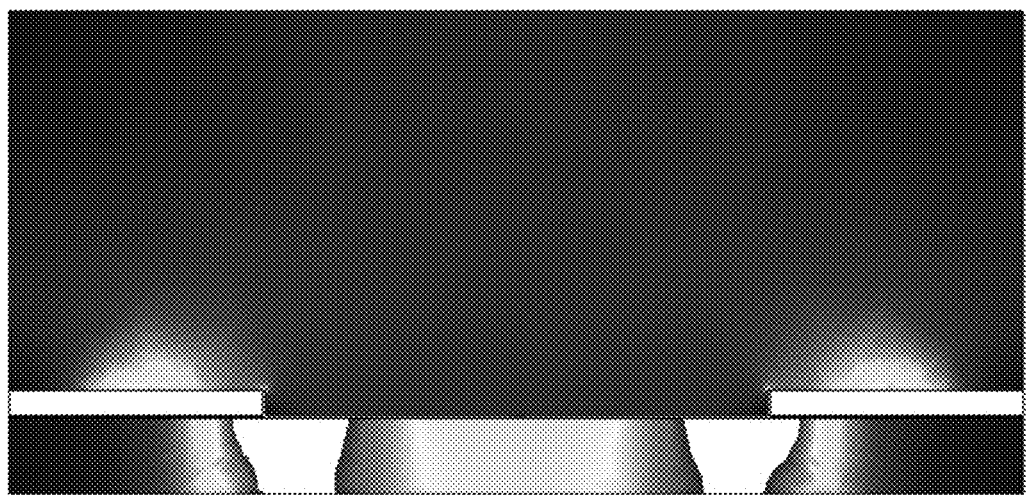

In a specific embodiment 50 shown in FIG. 4, the electrodes 14 comprise a 100-nm-thick indium-tin-oxide (ITO) layer 52 on a glass substrate 16, topped by a 50-nm-thick layer 54 of highly doped hydrogenated amorphous silicon (a-Si:H), and a 1-µm-thick layer 56 of intrinsic a-Si:H. Alternative materials can be used as long as they retain the indicated material properties shown in FIG. 3 (i.e., conductive or photosensitive).

In one embodiment, the inventive LOET device utilizes 10-µm-wide electrodes, with a 20-µm gap 46 between electrodes. However, other electrode sizes and gaps between the electrodes may be utilized.

Referring now to FIG. 3, FIG. 5 and FIG. 6, various alternative configurations of the generalized LOET structure can be utilized to improve the electric field characteristics of the LOET device. For example, in the embodiment 60 shown in FIG. 5A, the conductive layer 42 may be undercut. In the embodiment 70 shown in FIG. 5B, the conductive layer 42 is enveloped by the photosensitive material 44. In the embodiment 80 shown in FIG. 5C, the conductive layer 42 is passivated with a thin insulating layer 82 in the gaps between the electrodes. In the embodiment 90 shown in FIG. 5D, the conductive layer 42 is passivated by filling the electrode gaps with an insulating material 92. FIG. 6A and FIG. 6B show schematic diagrams of LOET electrode configurations corresponding to FIG. 5B and FIG. 5D, respectively.

Example 3

Referring to FIG. 7, illumination of the electrodes in the inventive LOET structure and various embodiments described above causes actuation of OET force, as in a conventional OET device. Significantly, however, as illustrated by FIG. 7, the electric field in the inventive LOET device is parallel to the plane of the electrodes for electrodes that have no undercut of the conductive layer as shown in FIG. 7A, electrodes with an undercut conductive layer as shown in FIG. 7B, electrodes with a conductive layer enveloped by photosensitive layer as shown in FIG. 7C, and electrodes with a thin insulating passivation layer in the gap between the electrodes as shown in FIG. 7D. In FIG. 7A, the high-electric-field regions at the edge of the electrodes are undesirable—the regions above the center of the electrodes are the desired high-electric-field regions. FIG. 7B through FIG. 7D show that the corresponding designs reduce the electric field at the electrode edges.

Example 4

Figure 8A:
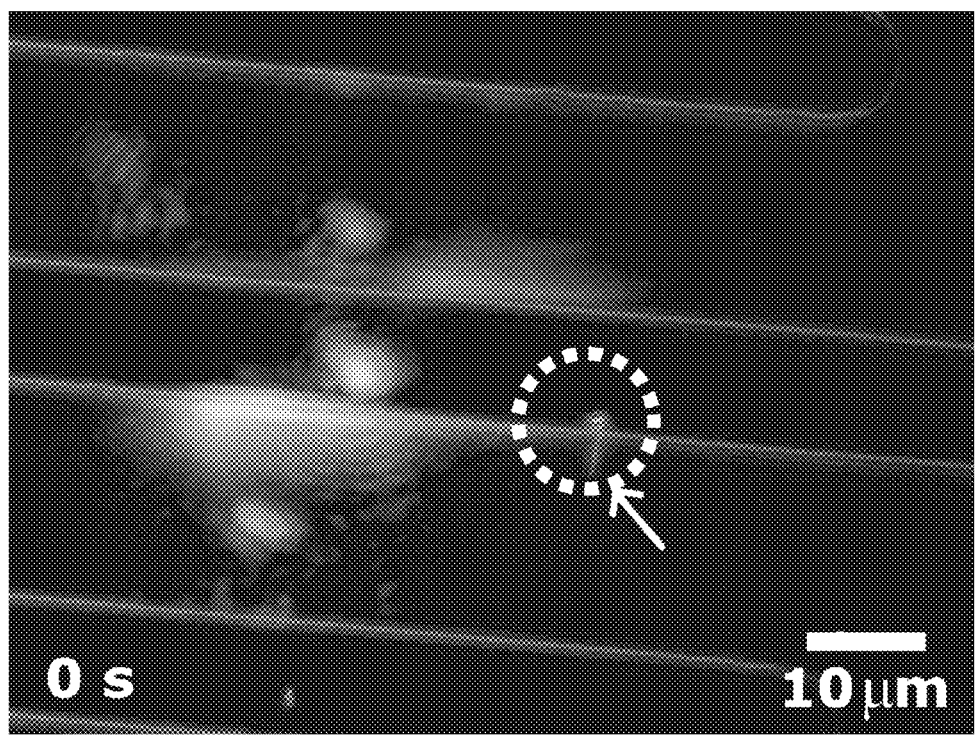
Figure 8B:
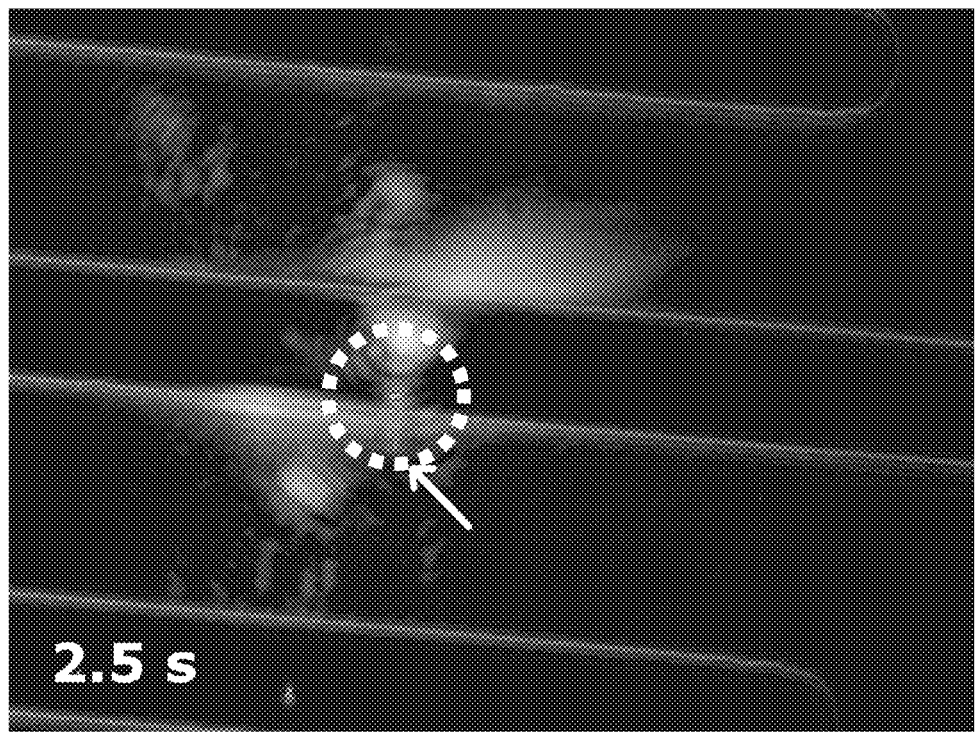

Referring to FIG. 8, we have demonstrated the trapping and transport of semiconductor nanowires (100-nm-diameter silicon nanowires) using a LOET device according to the invention. FIG. 8A shows a 100-nm-diameter, 5-µm-long silicon nanowire (circled) positioned near a LOET electrode. FIG. 8B shows that the nanowire is attached toward the laser spot and trapped.

Example 5

Figure 9B:
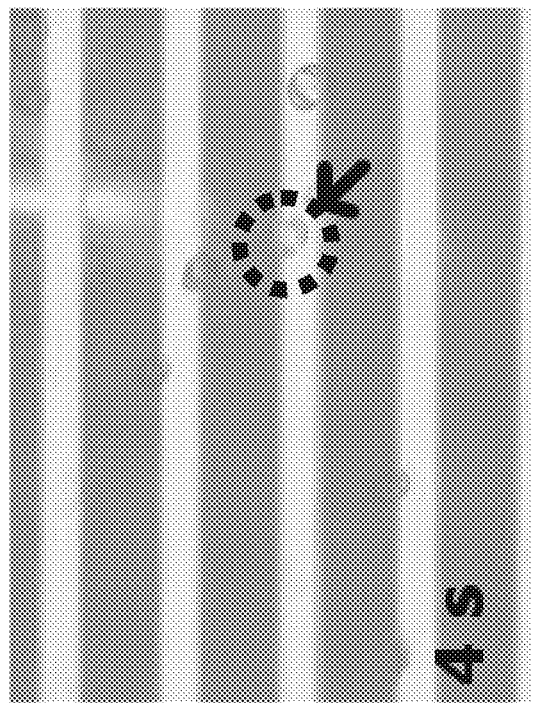
Figure 9A:
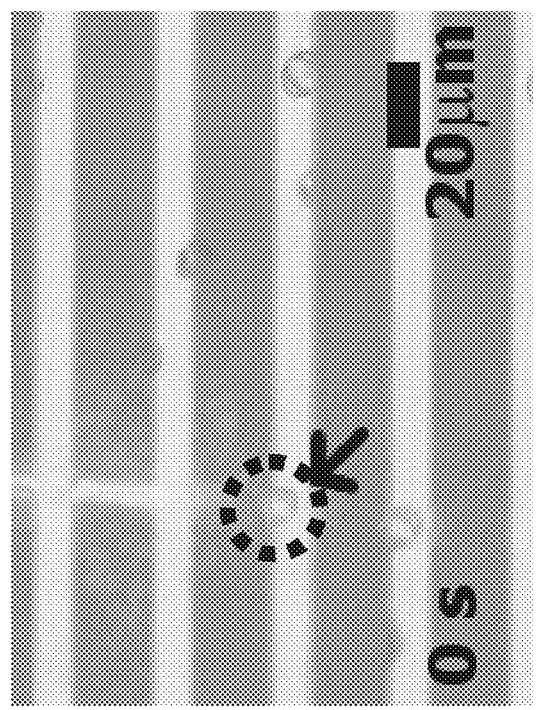

We have also transported live Jurkat cells in the LOET device as illustrated in FIG. 9. FIG. 9A shows a Jurkat cell (circled) trapped at the lower edge of the laser line. FIG. 9B shows that the cell is transported by moving the laser line toward the right.

Referring now to FIG. 10 through FIG. 12, an embodiment 100 of a LOET device is shown with a conductive opposing layer 102. In addition to operation as a lateral-field, single-sided device, we can also operate the LOET device with a conductive opposing layer (FIG. 10), or as a conventional OET device (FIG. 11). The conductive opposing layer can be grounded or floating.

Example 6

Figure 12B:
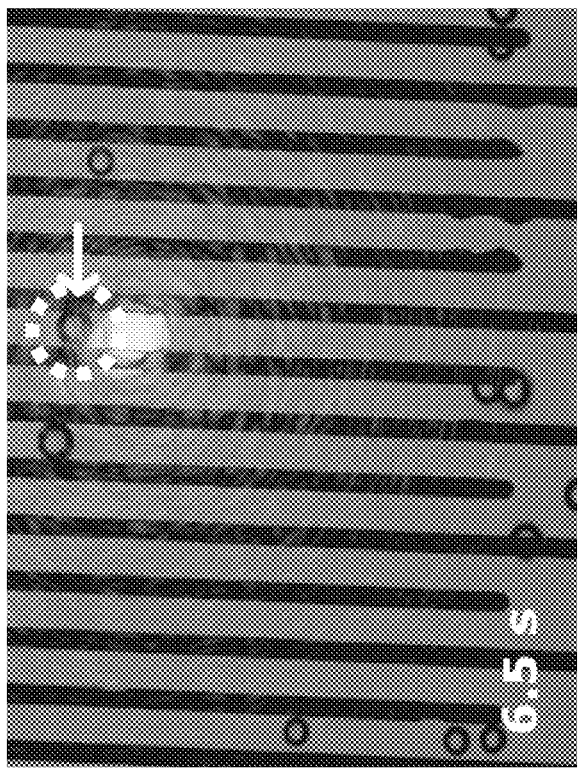
Figure 12A:
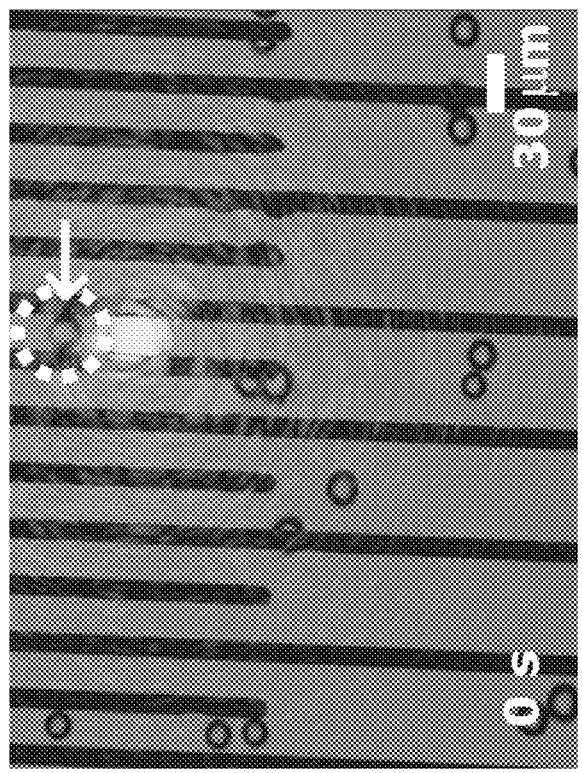

FIG. 12 illustrates manipulation of 20-µm-diameter polystyrene beads in a LOET configured for conventional OET operation. In FIG. 12A, a 20-µm-diameter polystyrene bead (circled) is pushed upwards by a laser spot. In FIG. 12B, the same bead is shown after being pushed upwards by the laser spot.

Referring to FIG. 13, photosensitive electrodes can also be used to create traveling electrical waves in the LOET device, by applying voltages of alternating phase to adjacent electrodes. FIG. 13 illustrates an embodiment 110 of a traveling-wave OET device, using alternating-phase voltages applied to photosensitive electrodes 14a (0°), 14b (90°), 14c (180°), 14d (270°) to produce a spatially-varying electric field. As shown in FIG. 14, the traveling electrical waves can also be created by patterning a conductive electrode layer which sandwiches the liquid layer and applying alternating-phase voltage to the patterned upper electrode surface. The OET device 112 can be a conventional OET device, a LOET device, or a traveling-wave OET device.

FIG. 15A illustrates automated parallel assembly of nanowires using an embodiment 120 of a LOET "trap" according to the present invention. In the embodiment 120 shown, an insulating substrate 122 (e.g., glass) is coated with a photosensitive layer 124. Metal electrodes 126a, 126b are patterned on the photosensitive layer. The metal electrodes may be coated with an electrical insulating layer if desired. This embodiment of the LOET device creates optically-defined electrically-conductive paths in the photosensitive layer 124 between the metal electrodes 126.

Light from a source 128 is patterned by a digital micromirror device (DMD) or other optical pattern generator 130. A personal computer 132 or the like is used to control the DMD pattern. The light pattern 134 is then focused onto the photoconductive substrate by an objective lens 136. The light pattern 134 can be used create "virtual electrodes" which extend from the metal electrodes 126a, 126b concentrating the electrical field into the gap 138 in the light pattern. The nanowire 140 is attracted to the high electric field gradients in this gap by dielectrophoresis.

FIG. 15B illustrates a large array 150 of LOET traps 120 that operate at the same time through computer-controlled DMD patterns.

Figures 16A, 16B, 16C:
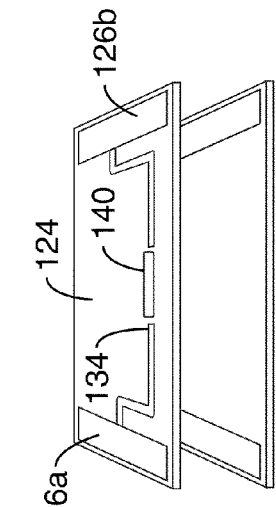
Figures 16D, 16E, 16F:
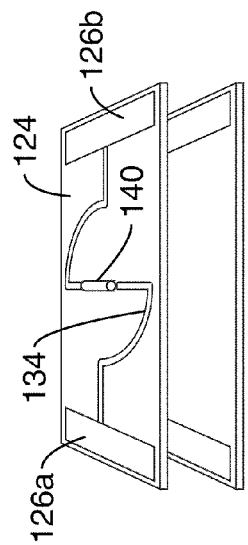

FIG. 16 shows the LOET trap 120 from FIG. 15 and how changing the light pattern 134, which acts as "virtual electrodes", can change both the position and the orientation of the nanowire 140. The high electrical field gradients created at the tips of the light pattern attract the nanowire by positive DEP, then by changing the light pattern the nanowire can be moved to any position in the x and y directions (FIG. 16A through FIG. 16C) and to any orientation in the x-y plane (FIG. 16D through FIG. 16F).

Example 7

The high electrical gradient force at and near the area defined by the optical patterns enables the trapping, transport, and rotation of particles such as, but not limited to, nanowires 140. In one embodiment, this configuration has been demonstrated using a silicon substrate 122 coated with a 1-μm-thick silicon dioxide layer (insulating layer). In this embodiment, the photosensitive layer 124 consisted of a 1.5-μm-thick amorphous silicon layer deposited on the silicon dioxide using plasma-enhanced chemical vapor deposition. Aluminum electrodes 126 that were 100 nm thick were created on the amorphous silicon layer using a lift-off process and electron-beam evaporation. Other metals or conductors may be used instead of aluminum. The aluminum electrodes were 50 μm in width, but this can vary. The spacing between the interdigitated aluminum electrode fingers can vary, but we have used a spacing of 25 μm to 200 μm. The interdigitated arrays terminated at two separate pads for external biasing. The aluminum electrodes can be coated with an insulating material. This material can be photoresist or silicon dioxide, as well as other insulators. In this example, the electrodes were coated with a 1-μm-thick dielectric layer. An AC bias was applied across pairs of aluminum electrodes.

Figure 17A:
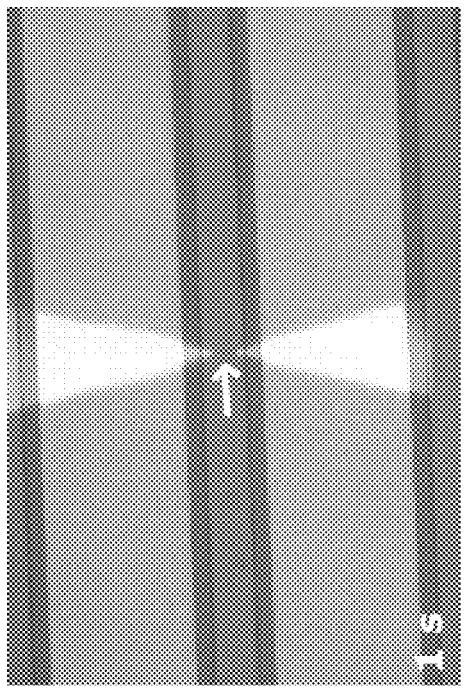
Figure 17B:
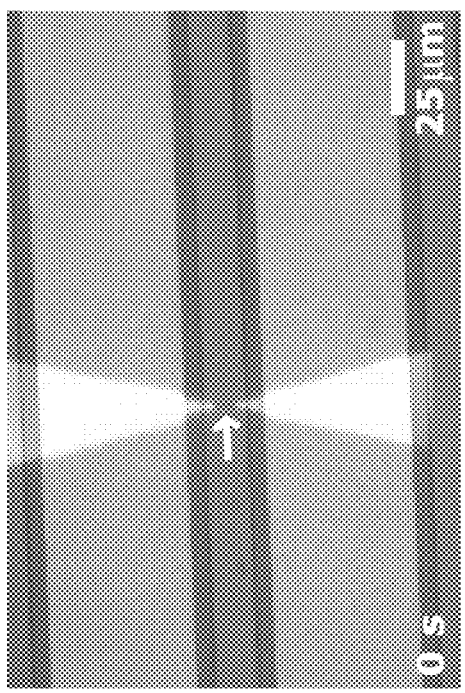
Figure 17C:
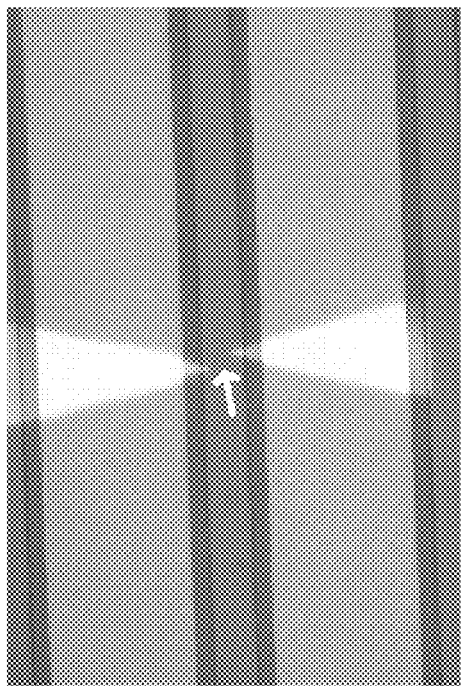

We demonstrated nanowire trapping, transport, and rotation with this device as illustrated in FIG. 17. FIG. 17A shows trapping of a nanowire between the gap created by the optical pattern. FIG. 17B shows that the nanowire has been transported to another area by moving the optical pattern. FIG. 17C shows that nanowire is rotated by adjusting the optical pattern.

This is just one embodiment of the device; varying layer thickness and dimensions will also work. Referring again to FIG. 10, the device can have a chamber 18 above it, containing the particles of interest. This chamber can be capped by glass or plastic 22, or by a conductive material 102 such as ITO. If a conductive material is used, it is possible to obtain another dimension of orientation control of particles such as nanowires (FIG. 18). For example, FIG. 18 illustrates vertical orientation control. The top electrodes are grounded, and the right bottom electrodes are connected to +V. The nanowire's vertical angle can be controlled by the voltage bias on the left electrode: (a) +V, (b) 0V, and (c) −V.

2. Phototransistor-Based Optoelectronic Tweezers (PhOET) for Highly Conductive Solutions We have previously demonstrated the manipulation of red and white blood cells and HeLa cells, as well as the selective concentration of live human B cells from dead cells. However, state of the art OET devices have only been demonstrated in a low-conductivity solution (<0.1 S/m). In low conductivity media, salt is replaced by osmotically-equivalent amounts of non-electrolytes; these media are non-physiological and eventually reduce cell. It also prevents certain biological applications, such as cell culturing.

Previously, OET devices used amorphous silicon (a-Si) as the photoconductive layer, which has a low photoconductivity. In contrast, a PhOET device according to an aspect of the invention utilizes a phototransistor built on single crystalline silicon to increase the optical gain; therefore, it could drive more conductive solution than an amorphous silicon OET device.

The normalized photoconductivity measurement an inventive phototransistor-based OET (PhOET) device and an amorphous silicon (a-Si) based OET are shown in FIG. 19. As illustrated by FIG. 19, a PhOET according to the present invention has an optical gain of more than ten-times higher than amorphous silicon at an optical density of 1 W/cm$^2$. A PhOET therefore reduces the required power for OET manipulation in high-conductivity solution. High optical power requirement reduce the effective manipulation area, and it may induce adverse effects in biological systems, such as excess heating. A PhOET demands less optical power, and therefore is more desirable for manipulation in highly conductive solutions.

An exemplary PhOET device structure 200 is shown in FIG. 20. The liquid containing the cells or particles 20 is sandwiched between an ITO-coated glass 202 and a bottom photoconductive surface 204. Here, a plurality of phototransistors 206 built on single crystalline silicon were used as the photoconductive layer. As illustrated, each individual phototransistor is isolated by a photoresist (PR) dielectric 208. In the embodiment shown, each phototransistor has a vertical bipolar junction transistor structure: from top to bottom, a highly doped n-type emitter layer 210, a moderately doped p-type base layer 212, and a low to moderately doped n-type layer 214 as both the collector and the conductive substrate. To operate the device, an AC signal is applied to the silicon substrate and the ITO-coated glass. When projected light illuminates on the photoconductive layer, it turns on the virtual electrodes, creating non-uniform electric fields and enabling particle manipulation via DEP forces.

An embodiment 300 of a PhOET fabrication process is shown in FIG. 21. At step 302, a low to moderately doped n-type 10-20 Ω-cm silicon wafer 214 is used as the starting material. Boron implantation, followed by a drive-in step 304 is used to form the moderately-doped p-type base layer 212 of the phototransistor. An arsenic implantation and annealing at step 306 then forms a shallow highly doped n-type emitter layer 210. The individual phototransistors 206 are then defined by deep reactive ion etching at step 308, which creates isolation between transistors. Finally, at step 310, photoresist is used to define opening areas on top of the emitter surface.

Example 8

Figure 22C:
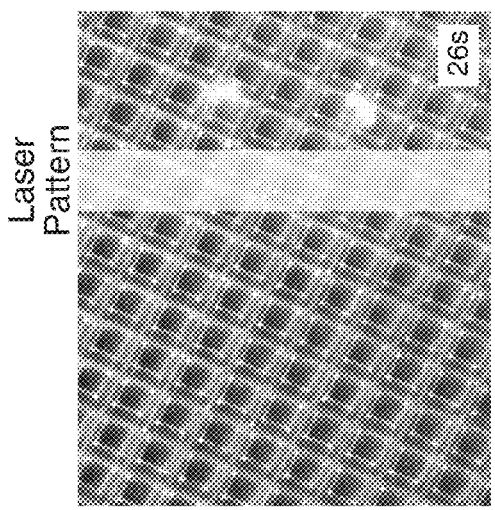
Figure 22B:
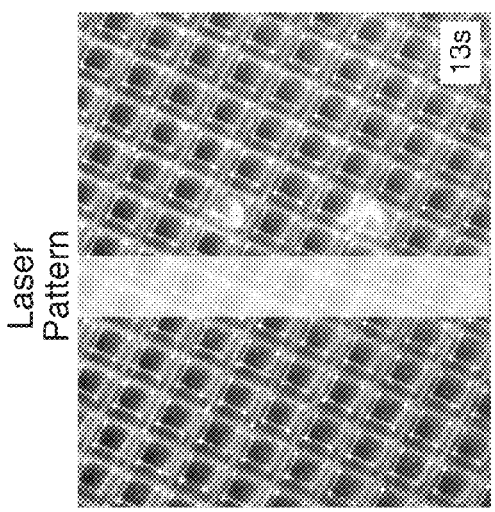
Figure 22A:
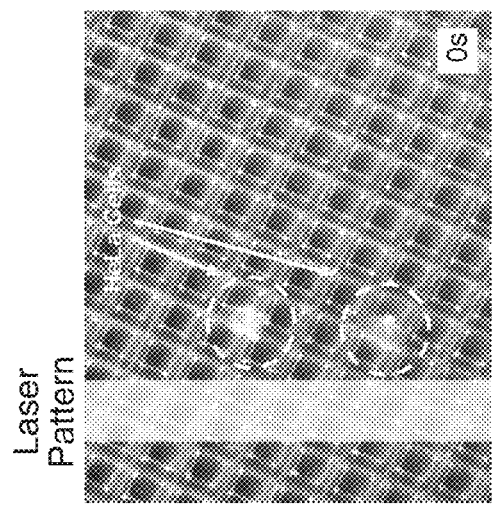

Referring to FIG. 22, we used a PhOET as described above to successfully manipulate HeLa and Jurkat cells in phosphate-buffered saline (PBS) solution and Dulbecco's Modified Eagle Medium (DMEM) solutions. Both solutions had conductivity of 1.5 S/m. In this experiment, a 16 $V_{pp}$ square wave AC signal with −2 VDC bias was applied across ITO and silicon substrate. A line-shaped optical pattern with a spot dimension of 50 μm×500 μm was projected onto the substrate and used to transport the cells across the field of view. Both types of cells experienced a repulsive force in the highly conductive solutions, and therefore were pushed away from the projected light. FIG. 22A through FIG. 22C show the cell movement as a function of time, namely 0 s, 12 s, and 26 s, respectively. The average cell velocities as a function of projected light intensity are shown in FIG. 23, with FIG. 23A showing results in the PBS solution and FIG. 23B showing results in the DMEM solution. We found that, using an intensity of 16 W/cm$^2$, HeLa cells can be transported at a speed of 10 μm/s, while Jurkat cells have movement speed of 8 μm/s. Note also that, while a PhOET is effective in operating in highly conductive solution, it also works effectively in lower conductivity solutions.

As can be seen, therefore, we have developed a new device that will enable optical manipulation of biological cells in highly conductive physiological buffers such as PBS and DEMS. Utilizing the high optoelectronic gain in phototransistors and the high mobility in single crystalline materials, we have demonstrated cell trapping and transport in phosphate buffered saline (PBS) and Delbecco's modified eagle medium (DMEM), the two most commonly used physiological solutions. Note that we have successfully preformed PhOET operation in highly conductive media (with conductivity of ~1.5 S/m) but PhOET also works effectively in lower conductivity solutions.

Referring now to FIG. 24, in addition to using single crystalline silicon, PhOET devices according to the present invention can be built using other semiconductor materials, such as poly-silicon and amorphous silicon.

For example, FIG. 24A shows a phototransistor structure 400 having an n-type substrate/collector 402, a p-type base region 404, and an emitter region 406 that is n+ polysilicon. Individual transistors are separated by photoresist dielectric regions 408.

FIG. 24B shows a phototransistor structure 500 having a n$^+$-p-n$^+$ geometry where the collector and emitter are interchangeable depending on the polarity of voltage applied. This structure comprises a substrate 502, an n+ collector/emitter 504, a p-type base 506, and an n+ emitter/collector 508. Individual transistors are separated by photoresist dielectric regions 510.

FIG. 24C shows a phototransistor structure 600 on a low resistivity substrate 602 with an n-type collector layer 604, p-type base layer 606, and n+ emitter layer 608. Individual transistors are separated by photoresist dielectric regions 610.

FIG. 24D shows a phototransistor structure 700 where isolation is achieved with a doping design that results in a planar device surface. This embodiment comprises an n-type substrate/collector 702, a p-type base layer 704, and an n+ emitter layer 706 where individual emitters are isolated by using ion implantations to form a planar device surface.

These structures can be realized using ion implantation and/or epitaxial growth, together with photolithography. A heterojunction phototransistor may provide higher current gain and faster response time.

In one embodiment, the phototransistors are pixilated into 20 μm by 20 μm squares with 2 μm gaps. Photoresist is used to define a 16 μm by 16 μm square opening on top of the emitter surface. It also passivates the exposed sidewalls. Other pixel size, gap size and opening windows can be used. The pixels can also be in other shapes, such as circular, rectangular, and line-shaped geometry. In addition to photoresist (PR), other dielectrics can be used to passivate the device. For example, silicon dioxide is an easy substitution as the dielectric layer.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

What is claimed is:

1. A planar optoelectronic tweezers apparatus, comprising:
a first electrode; and
a second electrode;
said first and second electrodes spaced apart by a gap;
said first and second electrodes supported by a substrate layer;
each said electrode comprising a conductive layer adjacent to said substrate layer and a photosensitive layer adjacent to said conductive layer;
wherein said electrodes are configured to create optically-induced dielectrophoretic forces in an electric field that is parallel to the plane of the apparatus.

2. An apparatus as recited in claim 1, wherein said conductive layer undercuts said photosensitive layer.

3. An apparatus as recited in claim 1, wherein said photosensitive layer surrounds said conductive layer.

4. An apparatus as recited in claim 1, further comprising a thin insulating layer around said conductive layer.

5. An apparatus as recited in claim 1, further comprising an insulating layer around said conductive layer and filling said gap.

6. A planar optoelectronic tweezers apparatus, comprising:
a first planar array of photosensitive electrodes;
a second planar array of photosensitive electrodes;
wherein electrodes in said first electrode array are spaced apart from electrodes in said second electrode array by an electrode gap;
a substrate layer supporting said first and second electrode arrays;
each said electrode comprising a conductive layer adjacent to said substrate layer and a photosensitive layer adjacent to said conductive layer; and
a cover layer spaced apart from and positioned adjacent said photosensitive layer, whereby a chamber for containing a liquid/particle solution is formed;
wherein said electrode arrays are configured to create optically-induced dielectrophoretic forces in an electric field that is parallel to the plane of the apparatus.

7. An apparatus as recited in claim 6, wherein said conductive layer undercuts said photosensitive layer.

8. An apparatus as recited in claim 6, wherein said photosensitive layer surrounds said conductive layer.

9. An apparatus as recited in claim 6, further comprising a thin insulating layer around said conductive layer.

10. An apparatus as recited in claim 6, further comprising an insulating layer around said conductive layer and filling said electrode gap.

11. An apparatus as recited in claim 6, further comprising a second conductive layer between said chamber and said cover layer.

12. A planar optoelectronic tweezers apparatus, comprising:
    a first planar array of photosensitive electrodes;
    a second planar array of photosensitive electrodes;
    wherein electrodes in said first electrode array are spaced apart from electrodes in said second electrode array by an electrode gap;
    wherein electrodes in said first electrode array and electrodes in said second array are interdigitated;
    a substrate layer supporting said first and second electrode arrays;
    each said electrode comprising a conductive layer adjacent to said substrate layer and a photosensitive layer adjacent to said conductive layer; and
    a cover layer spaced apart from and positioned adjacent said photosensitive layer, whereby a chamber for containing a liquid/particle solution is formed;
    wherein said electrode arrays are configured to create optically-induced dielectrophoretic forces in an electric field that is parallel to the plane of the apparatus.

13. An apparatus as recited in claim 12, wherein said conductive layer undercuts said photosensitive layer.

14. An apparatus as recited in claim 12, wherein said photosensitive layer surrounds said conductive layer.

15. An apparatus as recited in claim 12, further comprising a thin insulating layer around said conductive layer.

16. An apparatus as recited in claim 12, further comprising an insulating layer around said conductive layer and filling said gap.

17. An apparatus as recited in claim 12, further comprising a second conductive layer between said chamber and said cover layer.

18. A planar optoelectronic tweezers apparatus, comprising:
    a photosensitive layer on an insulating substrate;
    a first electrode; and
    a second electrode;
    said first electrode and second electrode spaced apart by a gap;
    said first and second electrodes supported by the photosensitive layer that is adjacent to said substrate;
    wherein said electrodes are configured to create optically-induced dielectrophoretic forces in an electric field that is parallel to the plane of the apparatus.

19. An apparatus as recited in claim 18, further comprising an insulating layer encapsulating the electrodes.

20. A planar optoelectronic tweezers apparatus, comprising:
    a photosensitive layer on an insulating substrate;
    a first planar array of electrodes;
    a second planar array of electrodes;
    wherein electrodes in said first electrode array are spaced apart from electrodes in said second electrode array by an electrode gap;
    said photosensitive layer supporting said first and second electrode arrays; and
    a cover layer spaced apart from and positioned adjacent said photosensitive layer, whereby a chamber for containing a liquid/particle solution is formed;
    wherein said electrode arrays are configured to create optically-induced dielectrophoretic forces in an electric field that is parallel to the plane of the apparatus.

21. An apparatus as recited in claim 20, further comprising an insulating layer encapsulating the electrodes.

22. A planar optoelectronic tweezers apparatus, comprising:
    a photosensitive layer on an insulating substrate;
    a first planar array of electrodes;
    a second planar array of electrodes;
    wherein electrodes in said first electrode array are spaced apart from electrodes in said second electrode array by an electrode gap;
    wherein electrodes in said first electrode array and electrodes in said second array are interdigitated;
    said photosensitive layer supporting said first and second electrode arrays; and
    a cover layer spaced apart from and positioned adjacent said photosensitive layer, whereby a chamber for containing a liquid/particle solution is formed;
    wherein said electrode arrays are configured to create optically-induced dielectrophoretic forces in an electric field that is parallel to the plane of the apparatus.

23. An apparatus as recited in claim 22, further comprising an insulating layer encapsulating the electrodes.

24. A phototransistor optoelectronic tweezers apparatus, comprising:
    a cover layer;
    a substrate layer;
    a photoconductive layer between said cover layer and said substrate layer; and
    a liquid layer between said cover layer and said photoconductive layer;
    wherein said photoconductive layer comprises a phototransistor.

25. An apparatus as recited in claim 24, wherein said phototransistor has a vertical bipolar junction transistor structure.

26. An apparatus as recited in claim 24, wherein said phototransistor comprises:
    a low to moderately doped n-type material as both a collector and a substrate;
    a moderately doped p-type base layer over said n-type material; and
    a highly doped n-type emitter layer over said base layer.

27. An apparatus as recited in claim 24, wherein said phototransistor comprises:
    an n-type material as both a collector and a substrate;
    a p-type base layer over said n-type material; and
    a polysilicon $n^+$ emitter layer over said base layer.

28. An apparatus as recited in claim 24, wherein said phototransistor comprises:
    a substrate layer;
    an $n^+$ collector/emitter layer over said substrate layer;
    a p-type base layer over said collector/emitter layer; and
    an $n^+$ emitter/collector layer over said base layer.

29. An apparatus as recited in claim 24, wherein said phototransistor comprises:
    a low resistivity substrate layer;
    an n-type collector layer over said substrate layer;
    a p-type base layer over said collector layer; and
    an $n^+$ emitter/collector layer over said base layer.

30. An apparatus as recited in claim 24, wherein said phototransistor comprises:
    an n-type material as both a collector and a substrate;
    a p-type base layer over said collector layer; and
    an $n^+$ emitter/collector layer over said base layer.

31. A phototransistor optoelectronic tweezers apparatus, comprising:
  a cover layer;
  a substrate layer;
  a photoconductive layer between said cover layer and said substrate layer; and
  a liquid layer between said cover layer and said photoconductive layer;
  wherein said photoconductive layer comprises a plurality of phototransistors separated by a dielectric gap.

32. An apparatus as recited in claim 31, wherein each said phototransistor has a vertical bipolar junction transistor structure.

33. An apparatus as recited in claim 31, wherein each said phototransistor comprises:
  a low to moderately doped n-type material as both a collector and a substrate;
  a moderately doped p-type base layer over said n-type material; and
  a highly doped n-type emitter layer over said base layer.

34. An apparatus as recited in claim 31, wherein said phototransistor comprises:
  an n-type material as both a collector and a substrate;
  a p-type base layer over said n-type material; and
  a polysilicon $n^+$ emitter layer over said base layer.

35. An apparatus as recited in claim 31, wherein said phototransistor comprises:
  a substrate layer;
  an $n^+$ collector/emitter layer over said substrate layer;
  a p-type base layer over said collector/emitter layer; and
  an $n^+$ emitter/collector layer over said base layer.

36. An apparatus as recited in claim 31, wherein said phototransistor comprises:
  a low resistivity substrate layer;
  an n-type collector layer over said substrate layer;
  a p-type base layer over said collector layer; and
  an $n^+$ emitter/collector layer over said base layer.

37. A method of fabricating a phototransistor as recited in claim 33, comprising:
  providing a low to moderately doped n-type silicon wafer as a substrate;
  forming a moderately-doped p-type base layer over said silicon wafer by Boron implantation followed by a drive-in step;
  forming a highly doped n-type emitter layer over said base layer by arsenic implantation and annealing;
  defining individual phototransistors by deep reactive ion etching and creating gaps in said emitter layer, base layer and substrate; and
  defining opening areas on top of the emitter surface using photoresist or another dielectric in said gaps and on said emitter surface.

* * * * *